(12) United States Patent
Levin et al.

(10) Patent No.: US 6,241,703 B1
(45) Date of Patent: Jun. 5, 2001

(54) ULTRASOUND TRANSMISSION APPARATUS HAVING A TIP

(75) Inventors: Philip S. Levin, Thompson, CT (US); Jon Saltonstall, Norwell; Loi Nguyen, Brookline, both of MA (US); Warren Taylor, Cary, NC (US)

(73) Assignee: Angiosonics Inc., Morrisville, NC (US)

( * ) Notice: Subject to any disclaimer, the term of this patent is extended or adjusted under 35 U.S.C. 154(b) by 0 days.

(21) Appl. No.: 09/321,268

(22) Filed: May 27, 1999

Related U.S. Application Data

(63) Continuation-in-part of application No. 08/858,247, filed on May 19, 1997, now Pat. No. 5,971,949, which is a continuation-in-part of application No. 08/700,064, filed on Aug. 19, 1996, now Pat. No. 5,836,896.
(60) Provisional application No. 60/038,180, filed on Feb. 13, 1997.

(51) Int. Cl.[7] .................................................. A61B 17/32
(52) U.S. Cl. ........................................ 604/22; 606/169
(58) Field of Search ................................ 601/2; 604/22; 606/169

(56) References Cited

U.S. PATENT DOCUMENTS

| | | | | |
|---|---|---|---|---|
| 5,304,115 | * | 4/1994 | Pflueger et al. | 604/22 |
| 5,380,274 | * | 1/1995 | Nita | 604/22 |
| 5,713,848 | * | 2/1998 | Dubrul et al. | 604/22 |
| 5,876,369 | * | 3/1999 | Houser | 604/22 |
| 5,879,364 | * | 3/1999 | Bromfield et al. | 606/169 |
| 5,989,208 | * | 11/1999 | Nita | 604/22 |
| 5,989,271 | * | 11/1999 | Bonnette et al. | 606/159 |
| 5,989,275 | * | 11/1999 | Estabrook et al. | 606/169 |

* cited by examiner

Primary Examiner—Francis J. Jaworski
(74) Attorney, Agent, or Firm—Cowan, Liebowitz & Latman, P.C.; William H. Dippert

(57) ABSTRACT

An ultrasound transmission device for utilizing ultrasound energy ultrasound to treat intravascular conditions, such as stenotic and occluded regions of blood vessels, is provided. The ultrasonic transmission device includes a transmission member connectable to the ultrasound energy source on a one end and a tip on the other end. The tip includes a distal section, a proximal section and an intermediate section. The proximal section has a first diameter larger than the transmission member diameter. The intermediate section includes a decreasing step portion, a narrowed portion, and an increasing step portion.

32 Claims, 19 Drawing Sheets

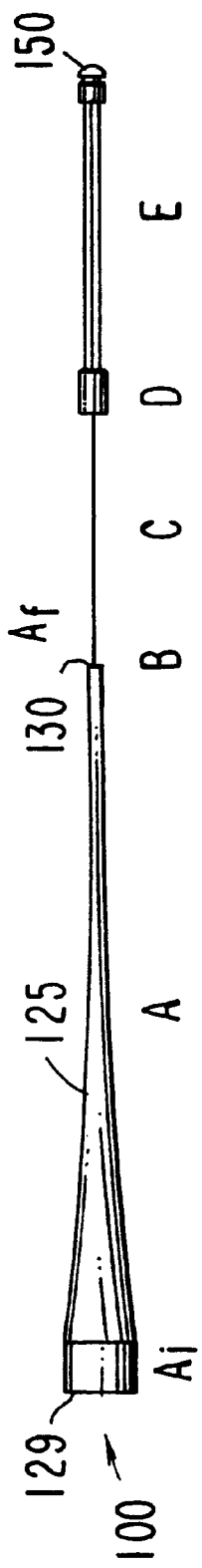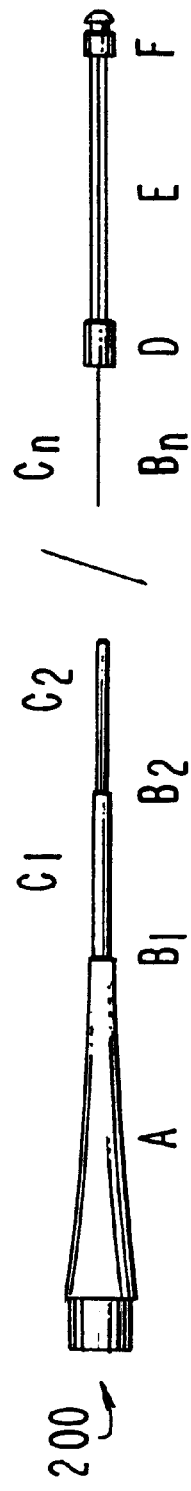
FIG.1
FIG.2

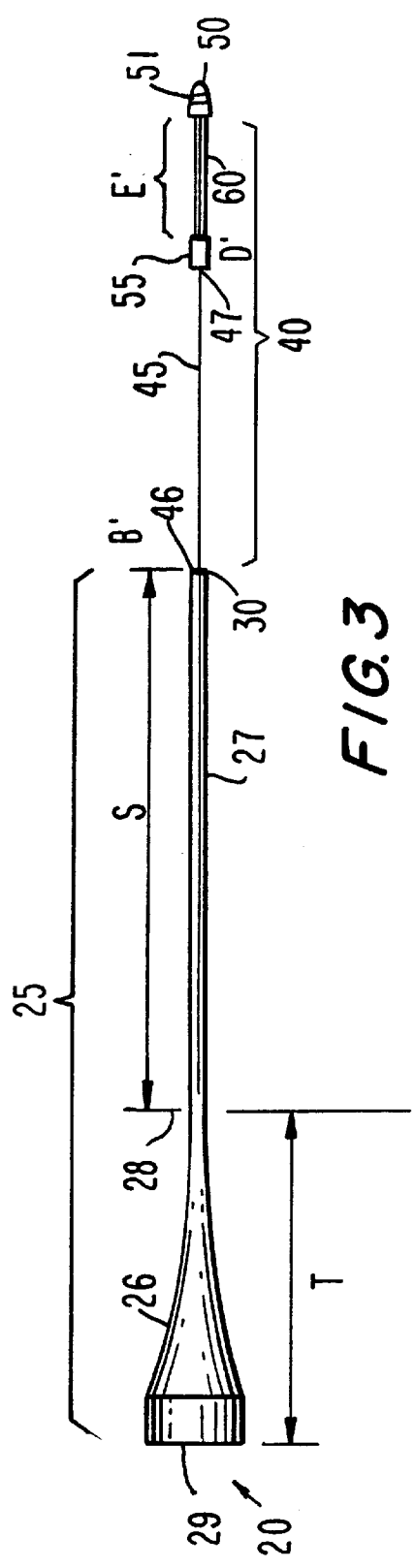
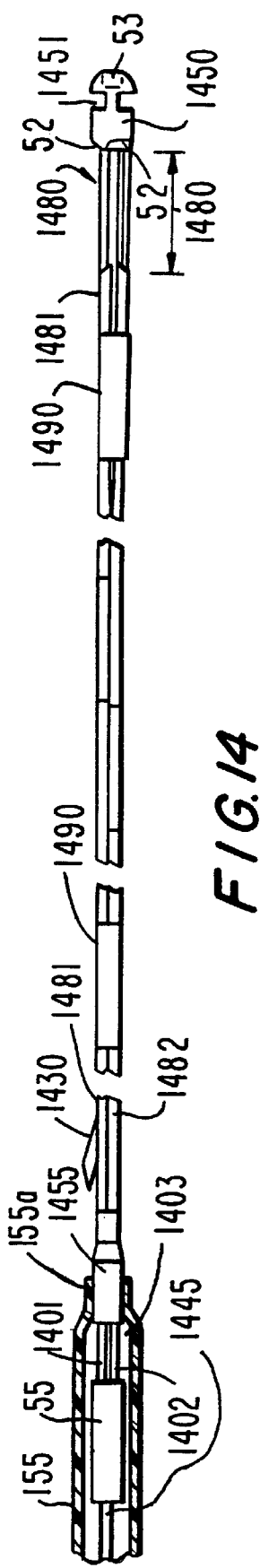

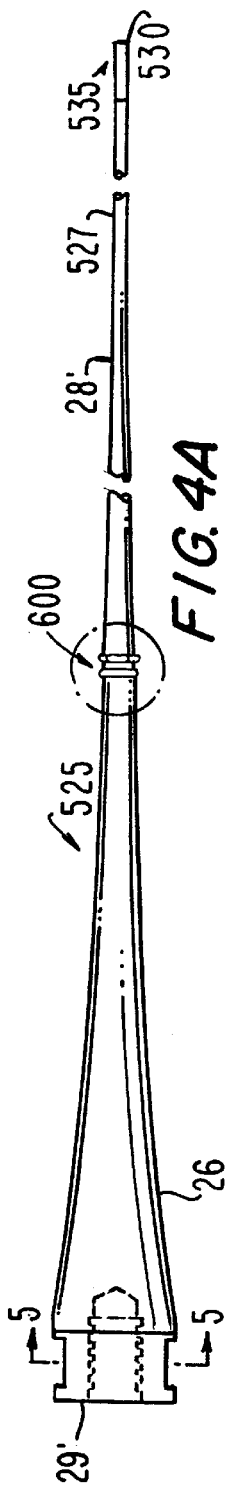
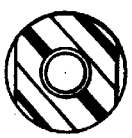
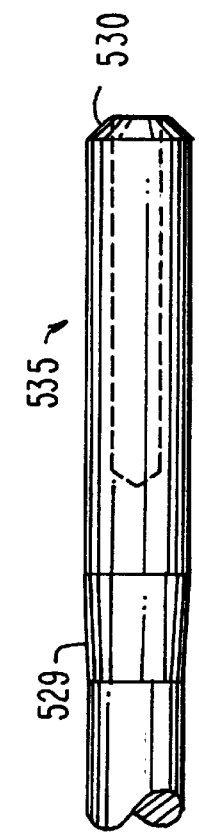
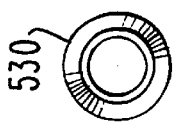
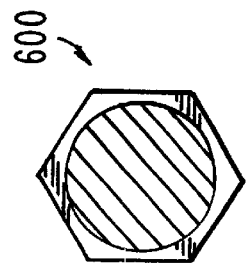
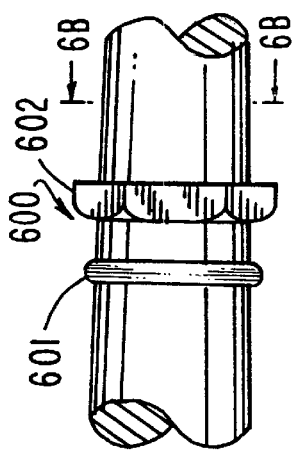

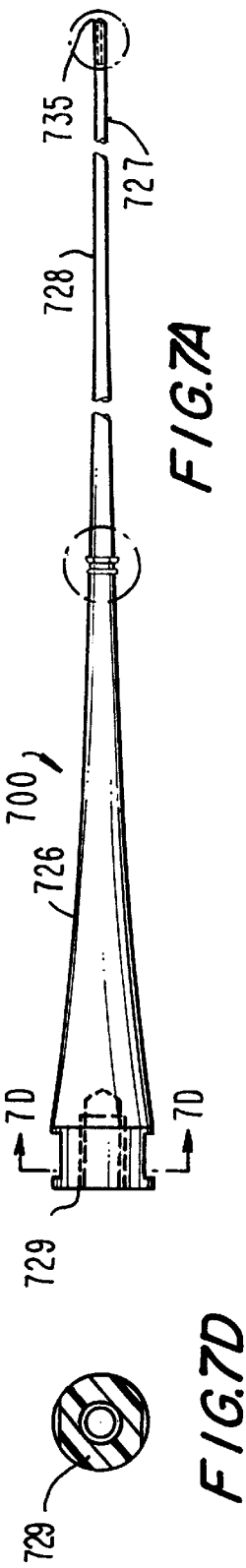
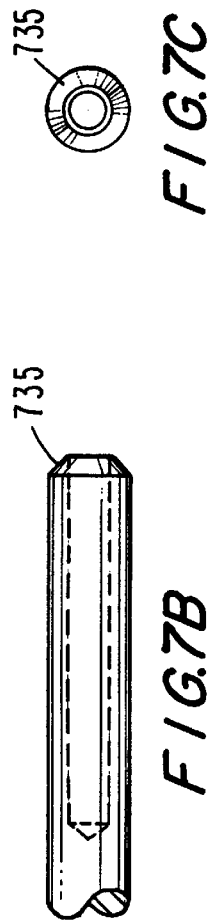
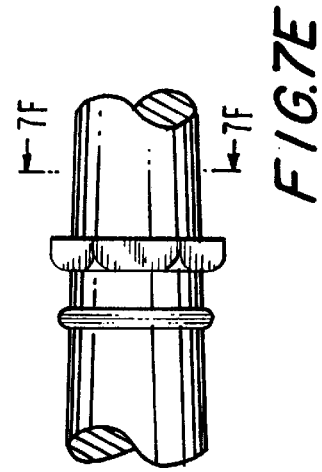
FIG.7A
FIG.7B
FIG.7C
FIG.7D
FIG.7E
FIG.7F

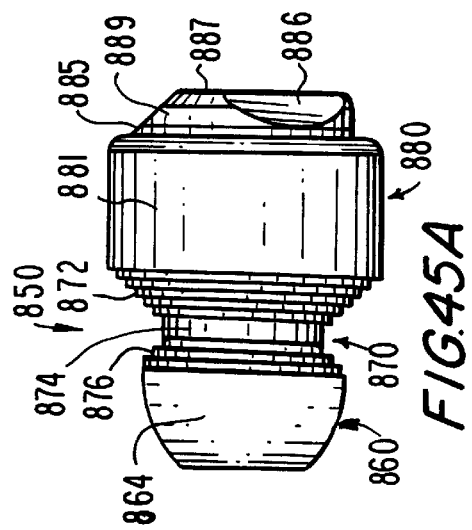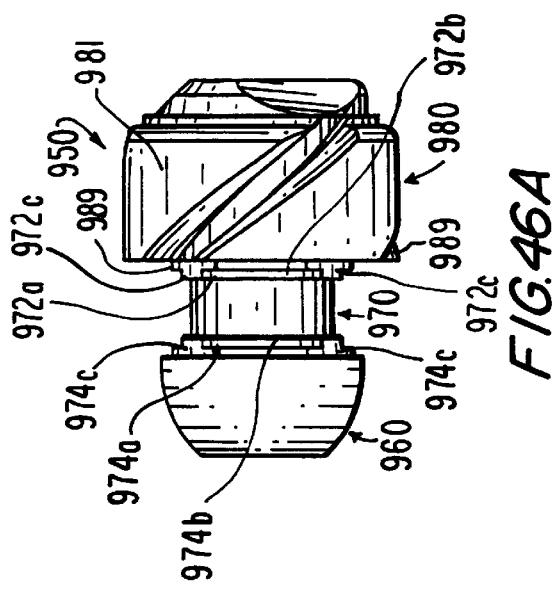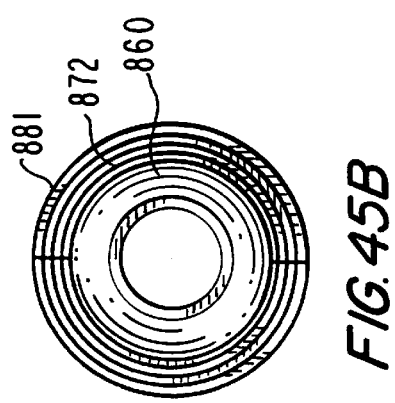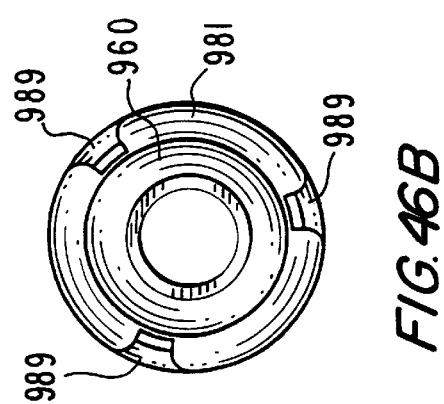

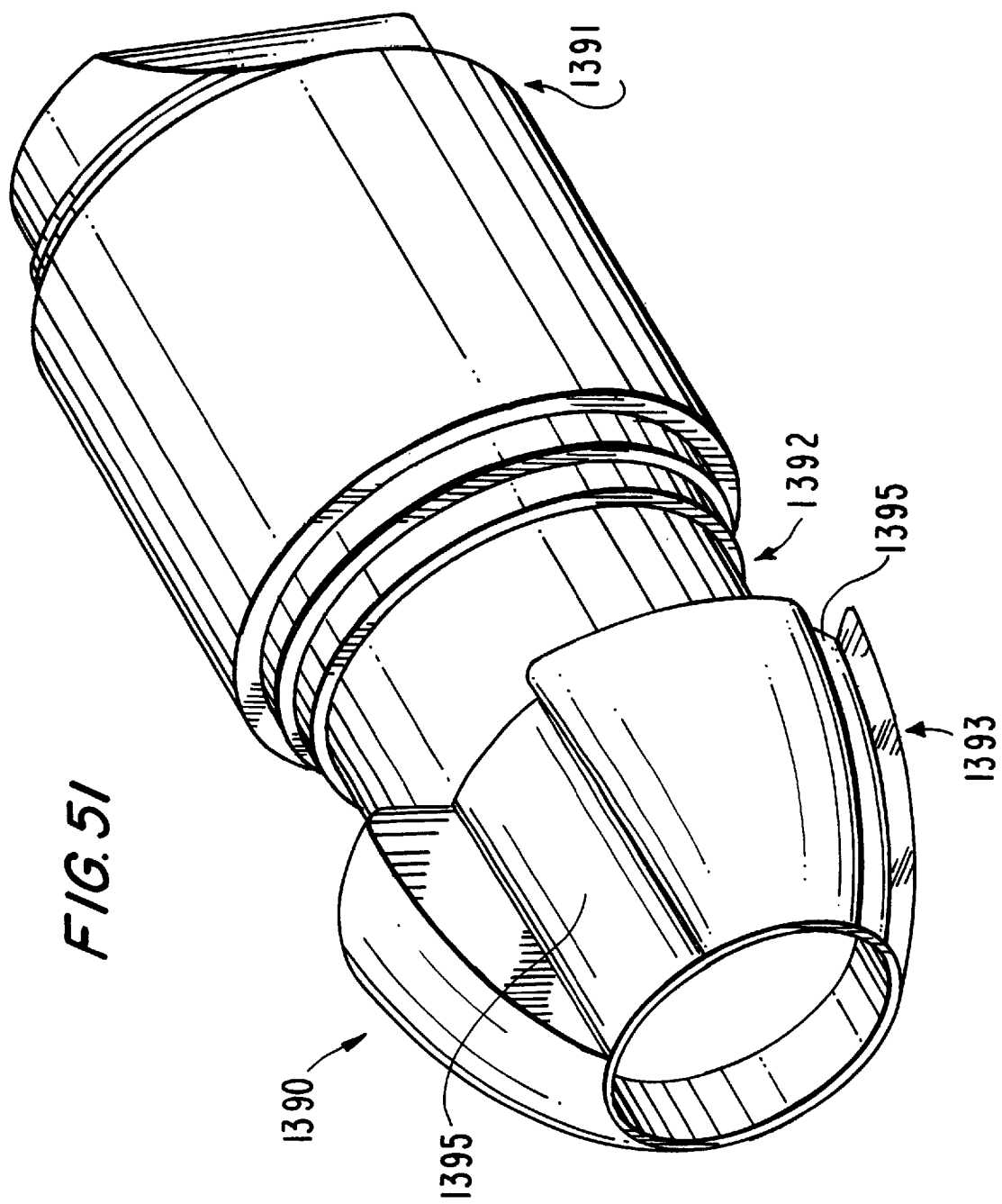

ULTRASOUND TRANSMISSION APPARATUS HAVING A TIP

CROSS REFERENCE TO RELATED APPLICATIONS

This application is a continuation-in-part of U.S. application Ser. No. 08/700,064, filed on Aug. 19, 1996 and now U.S. Pat. No. 5,836,896, and a continuation-in-part of U.S. application Ser. No. 08/858,247, filed on May 19, 1997 and now U.S. Pat. No. 5,971,949, which is a continuation-in-part of provisional U.S. application Ser. No. 60/038,180, filed Feb. 13, 1997, all of which are hereby incorporated by reference.

BACKGROUND OF THE INVENTION

The invention relates generally to medical devices and, more particularly, to an improved ultrasound probe and a method of using the improved ultrasound probe for treating conditions to such as stenotic or occlusive vascular disorders.

Stenotic or occluded arteries are commonly treated by using one or several methods, which include, balloon or laser angioplasty, atherectomy and bypass surgery. While these types of treatments have had some success, they each have undesirable side effects. For example, following a balloon angioplasty procedure, the stenosis often rebounds to again obstruct the s vessel; laser angioplasty and atherectomy procedures carry the risk of damaging the arterial structure; and bypass surgery is traumatic and requires a prolonged recovery period.

In recent years, a number of devices that use ultrasonic energy to ablate obstructive material from blood vessels have been described in U.S. patents, such as U.S. Pat. No. 4,870,953 (Don Michael), U.S. Pat. No. 4,920,954 (Alliger et al.), and U.S. Pat. No. 5,269,287 (Weng et al.), the contents of which are incorporated herein by reference. In general, ultrasound transmitting devices have been reasonably successful when used to ablate obstructions located in peripheral blood vessels, such as the femoral artery. However, conventional ultrasound devices have been shown not to be fully satisfactory. For example, in applications within smaller blood vessels, such as the distal sections of coronary arteries, successful applications have been harder to achieve in practice due in part to the more tortuous paths and smaller vessel diameters involved.

While a number of devices that use ultrasonic energy to ablate obstructive material from blood vessels have been described in recent years, very little has been written about methods of using such devices. One method of ablating material from blood vessels by using heat is disclosed in U.S. Pat. No. 4,773,413 (Hussein et al.), which is hereby incorporated by reference. A second U.S. patent, U.S. Pat. No. 5,324,255 (Passafaro et al.), describes a method of using ultrasound to treat vasospasm, the content of which is incorporated herein by reference. However, little has been written on a method of using ultrasound devices, apparently due to a general lack of success in providing a safe, effective ultrasonic device capable of ablating clots.

Accordingly, it is desirable to provide an improved device and method for the treatment of stenotic or occluded arteries and the like which overcomes shortcomings of the prior art.

SUMMARY OF THE INVENTION

Generally speaking, in accordance with the invention, an ultrasonic treatment system and method for utilizing ultrasound to treat stenotic and occluded regions of blood vessels and artificial vessels, such as grafts or shunts used by dialysis patients, are provided. The ultrasonic treatment system includes an ultrasonic probe, having a proximal and distal end, and an ultrasonic energy source. The distal end vibrates at ultrasonic frequencies at the treatment site when the energy source is applied to the proximal end. The amplitude of vibration is herein also referred to as displacement. A guide catheter may be provided, and the probe may be slidably disposed within the guide catheter. A guidewire may be provided and the probe may be slidably disposed over the guidewire. The probe may include a horn at the proximal end, a transmission member with a proximal and a distal end connected to the horn at the transmission member's proximal end, and a distal tip at the transmission member's distal end. The transmission member may include one or more co-axial transmission wires, having proximal and distal ends, connected serially.

One section of the transmission member may be formed with multiple transmission wires arranged in parallel. The diameter or cross-sectional area of the proximal end of each successive transmission wire, moving toward the distal end of the probe, whether the transmission wires are in series or in parallel, may be less than the cross-sectional area of the distal end of the preceding transmission wire.

The diameter or cross-sectional area of the proximal end of the initial transmission wire may be less than the diameter or cross-sectional area of the distal end of the horn. In accordance with the foregoing elements, a step-down in cross-sectional area can occur at the transition between the horn and the first transmission wire, successive transmission wires and elsewhere in the probe. Some or all of the step transitions should be located at or near displacement nodes (minima) in order to effect maximum displacement amplification and maximize the delivery of ultrasound energy to the distal working end of the device. Each step transition that is located at or near a displacement node is consequently located at or near a stress maximum. Therefore, this invention reaps the benefit gained from high displacement amplification at each step transition located at or near a displacement node because the design withstands the high stresses at these transitions.

It will be understood by those experienced in the art that both the frequency and wavelengths of resonance (or anti-resonance) of the probe and the associated standing wave developed along the probe may shift depending upon the tortuosity of the blood vessels to be treated. Thus, the various nodal and anti-nodal portions of the standing wave may shift as a probe is advanced, retracted, and manipulated in a blood vessel. It will be understood that the probe is designed in accordance with an average frequency and an average standing wave. More particularly, the placement of the standing wave nodes and anti-nodes relative to the structural elements of the probe are referenced herein to the average geometric conditions or tortuosity of the treatment application.

It is an advantage of this invention that the placement of one or more step transitions at or near displacement nodes will tend to reduce the probe's sensitivity to tortuosity, especially when the step transitions are located proximal of the most tortuous sections. Therefore, in accordance with another aspect of this invention, those step transitions which are placed at or near displacement nodes can be used to effectively reduce the probe's sensitivity to tortuosity.

It will be understood that the techniques for assembling the sections of this invention are equally applicable to systems that promote or focus ultrasound energy to enhance the absorption of drugs, induce apoptosis in cells, and/or treat tissue, tumors, obstructions, and the like, within and without the body, and in systems to be utilized for laproscopic surgery, for ultrasonic scalpels, and to induce tissue hyperthermia for cancer radiation therapy, for example.

Furthermore, it will be understood that while several examples given herein refer to intravascular applications of the invention employing guide catheters, introducer sheaths, guidewires, and the like, the invention is equally applicable to topical or superficial treatments, therapies administered in cavities of the body, intramuscular and intra-tissue treatments, including the application of ultrasound to fatty deposits to assist in their removal, the use of ultrasound to enhance healing, or to stimulate or suppress the functioning of bodily organs.

In accordance with another aspect of this invention, some or all of the step transitions are fashioned as joints wherein the same or different materials, selected for their particular advantageous properties, are joined to form the step transition. For example, an aluminum wire of a thick diameter may be joined to a higher strength titanium wire of a smaller diameter.

In accordance with another aspect of this invention, each step transition, which is fashioned as a joint, is designed as a high strength coupling. For example, a crimp joint may be used with enhanced strength by roughening the surface of one or all of the joining members.

In accordance with another aspect of this invention, there is provided a tip having a distal section, a proximal section and an intermediate section connecting the distal section and the proximal section. The proximal section can have a first diameter that is larger than the diameter of the transmission wire. The intermediate section can include a portion having steps of decreasing diameter, a narrowed portion and a portion having steps of increasing diameter. The distal section can have a second diameter, the second diameter being narrower than said first diameter. Preferably the distal section is formed generally as a hemispheroid, having a diameter larger than the intermediate section diameter.

In accordance with yet another aspect of this invention, there is provided an ultrasound transmission member having a moisture-blocking coating material. The transmission member coating serves to reduce or eliminate stress corrosion and may be formed of a variety of thin film coating materials, including hydrocarbon material, such as parylene. Parylene may be vacuum deposited so as to provide complete, microscopic coverage of the component, even as a thin film.

In accordance with another embodiment of the invention, a low friction sheathing material for the transmission member is provided that improves the transmissive qualities of the transmission member. The sheathing material is selected to minimize friction with the transmission member and may be formed of a flexible polymer material such as polyimide. Polyimide is a low friction, high temperature polymer that can be formed into tubes with extremely thin walls.

In accordance with another embodiment of the invention, the distal working end, or tip, of the device may be fashioned with an axial through-hole. A tubular assembly may be affixed within that hole and may be configured to be slidably disposed within a second tubular assembly positioned proximal of the first tubular assembly, so that a tubular piston-cylinder arrangement may be effected. Alternatively, the second tubular assembly positioned proximal of the first tubular assembly may be configured to be slidably disposed within the first tubular assembly. This piston-cylinder arrangement may then be utilized as a guidewire pathway with unique abrasion-resistant properties.

Accordingly, it is an object of the invention to provide an improved device for treating thrombosis, stenosis and the like.

Another object of the invention is to provide an improved ultrasound probe.

Still another object of the invention is to provide an ultrasound probe having improved flexibility, guidability and reduced diameter.

Yet another object of the invention is to provide an apparatus that is designed to maximize transmission of ultrasonic energy for a given application.

Still a further object of the invention is to provide an ultrasonic tip that prevents abrasion by a guidewire which is fed through a bore in the tip.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure. The scope of the invention will be indicated in the claims.

BRIEF DESCRIPTION OF THE DRAWINGS

For a fuller understanding of the invention, reference is had to the following description, taken in connection with the accompanying drawings, in which:

FIG. 1 is a side view of an ultrasound transmission device constructed in accordance with an embodiment of the present invention;

FIG. 2 is a side view of an ultrasound transmission device constructed in accordance with another embodiment of the invention;

FIG. 3 is a side view of an ultrasound transmission device constructed in accordance with another embodiment of the invention, having a straight transmission member, integral with the horn;

FIG. 4A is a side view of a horn of an ultrasound transmission device in accordance with an embodiment of the invention, having a straight transmission member, integral with the horn, a way of attaching a second transmission member at its distal tip, a way of attaching sheathing via a keyed o-ring groove section, and a way of attaching a transducer at its proximal end;

FIG. 4B is an enlarged view of the distal tip of the transmission member of FIG. 4A;

FIG. 4C is an end view of the distal tip of the transmission member of FIG. 4B.

FIG. 5 is a cross-sectional view taken along line 5—5 of FIG. 4A;

FIGS. 6A and 6B are side and end views, respectively, of a keyed O-ring groove section of the horn of FIG. 4A;

FIG. 7A is a side view of an additional embodiment of an ultrasound transmission member in accordance with an embodiment of the invention;

FIG. 7B is an enlarged view of the distal tip of the transmission member of FIG. 7A;

FIG. 7C is an end view of the distal tip of FIG. 7B;

FIG. 7D is a cross-sectional view taken along line 7D—7D of FIG. 7A;

FIGS. 7E and 7F are side and end views, respectively, of a keyed O-ring groove section of the horn of FIG. 7A;

FIG. 14 is an enlarged side view of a section of an ultrasound transmission device with a multiwire construction constructed in accordance with an embodiment of the invention;

FIGS. 42A–50A are side views of the distal tips of ultrasound transmission devices constructed in accordance with embodiments of the invention;

FIGS. 42B–44B are rear views of the distal tips of FIGS. 42A–50A;

FIGS. 45B–50B are front views of the distal tips of FIGS. 42A–50A;

FIG. 51 is a perspective view of a distal tip of the ultrasound transmission device constructed in accordance with embodiments of the invention.

DETAILED DESCRIPTION OF THE PREFERRED EMBODIMENTS

Figure 8:
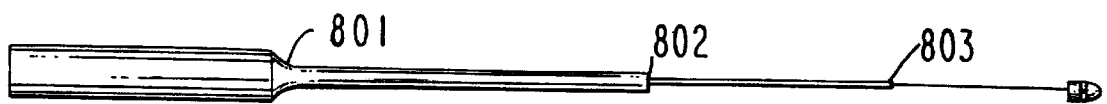
FIGS. 8–13, and 13A are side views of ultrasound transmission devices constructed in accordance with embodiments of the invention.

It has been determined that an effective way of ablating thrombus, occlusions and the like, is to use an ultrasound probe to deliver ultrasound energy to a selected area within a patient's vasculature. However, in order to reach relatively inaccessible areas of the vasculature, it is necessary to provide an extremely flexible device which is of adequate length and sufficiently guideable. In order to transmit sufficient power, it is desirable to receive ultrasound energy from an energy source with a probe having a relatively large diameter proximal end. However, large diameters lead to undesirable stiffness and insertion problems. Accordingly, to accomplish the foregoing objectives, an ultrasound probe is provided, which makes a rapid transition from the large diameter "horn" section that receives the ultrasound energy from an ultrasound source, to relatively thin and flexible transmission media, while minimizing the loss of transmission power, strength or guidability.

An improved ultrasound probe in accordance with an embodiment of the invention for accomplishing the foregoing is illustrated generally as probe 100 in FIG. 1. Probe 100 is formed with a tapered member horn section 125, formed with a proximal end 129 of diameter $A_i$ constructed to be coupled to a source of ultrasound energy (not shown). When coupled to a source of ultrasound energy, proximal end 129 is preferably located at a displacement maximum relative to the standing ultrasound wave supported by the overall device. Proximal end 129 may be coupled directly to a transducer or other energy source or to an intermediate member located between proximal end 129 and the energy source. From proximal end 129, tapered member 125 tapers, in section A thereof, to a reduced diameter distal end 130, of diameter $A_f$ at a transition zone B. Proximal end 129 must be large enough to receive sufficient energy to treat the thrombus, occlusions and the like. However, in order to provide optimal flexibility, it is desirable to reduce the diameter of distal portions of probe 100 as much as possible, while minimizing loss of energy, strength or guidability. Furthermore, the reduction in diameter must be accomplished in such a manner as to amplify, i.e. increase the amplitude of, the ultrasound vibrations.

Following tapered section A of distal diameter $A_f$ (or one or more tapered sections A), is a constant diameter section C, of diameter $C_i$, where $C_i < A_f$. In the event additional reductions in diameter are desired, a second transition zone D may be provided, for coupling section C to a section E of one or more lengths of transmission media, each of diameter $E_i$, where $E_i < C_i$.

Section C may be composed of a different material than section A. For example, section A may be composed of aluminum, which has superior ultrasound transmission properties, is easily machined and is inexpensive, while section C may be composed of titaniun, titanium alloys or other materials (including other metals, glass, ceramics, cermets, polymers and composites) that have adequate ultrasound transmission properties, but greater tensile strength for the smaller diameters required.

Figure 9:
Figure 40A:
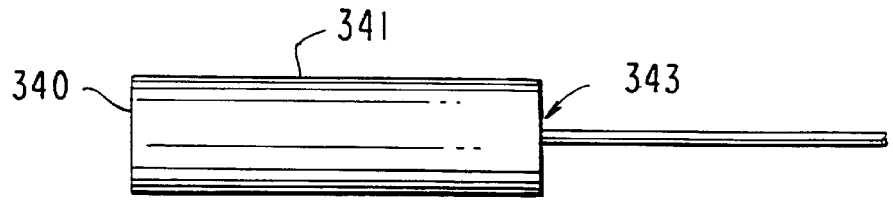
FIGS. 40A and 40B are schematic side views showing the relationship between wavelength and first transmission member length.
Figure 40B:
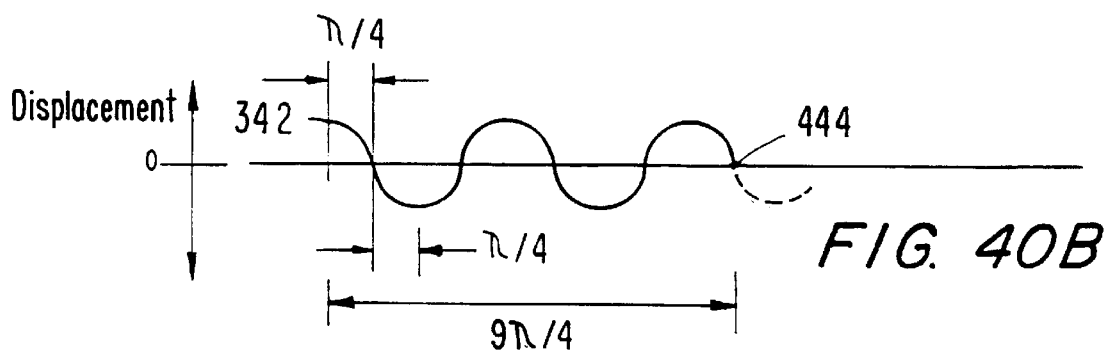
Figure 41A:
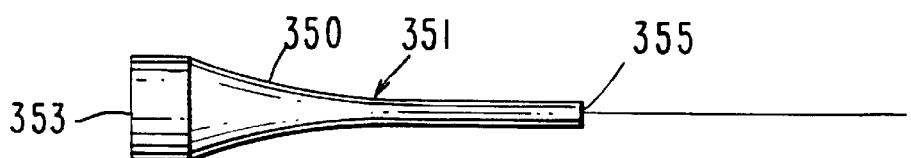
FIGS. 41A and 41B are schematic side views showing the relationship between wavelength and first transmission member length.
Figure 41B:
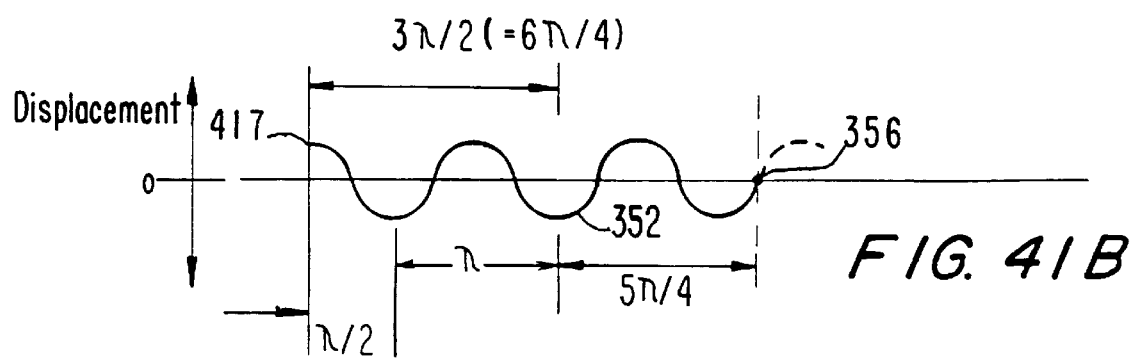

FIGS. 41A and 41B provide a simplified representation of a portion of a longitudinal standing wave that could be induced in section A of FIG. 1. Longitudinal displacement is plotted using the vertical axis of the figure and longitudinal position in section A is plotted along the horizontal axis. FIG. 41 A represents section A of FIG. 1 as composed of a first straight section, a second tapered section, which terminates at 351, and a final straight section, which terminates at 355. This arrangement is also shown in FIG. 3. Similarly, where section A of FIG. 1 is of a constant diameter, FIGS. 40A and 40B provide a simplified representation of a portion of a longitudinal standing wave that could be induced in that section. This arrangement is also shown in FIGS. 8 and 9.

It is advantageous for a step down in cross-sectional diameter to be located at a displacement minimum in order to obtain maximum amplification of displacement. Therefore, referring to FIGS. 40A and 40B, given that a proximal end 340 of a first medium 341 of wide diameter is at a displacement maximum 342, step downs in transmission media diameter, such as step down 343, are preferably located at displacement minimums 444, which will be located at odd multiples of $\lambda/4$. For illustrative purposes, in FIG. 40B, step down 343 is shown located at 9 $\lambda/4$. Similarly, as shown in FIGS. 41A and 41B, given that a proximal end 353 of a first medium 350 of wide diameter is at displacement maximum 417, step down 355 is preferably located at displacement minimum 356, at odd multiples of $\lambda/4$. For illustrative purposes, in FIG. 41B, step down 355 is shown located at 11 $\lambda/4$.

It is to be understood that FIGS. 40B and 41B are simplifications of a portion of the standing wave pattern. In actuality, the ultrasound wavelength is a function of the shape, dimensions and material of the horn and probe. Therefore, the wavelength is not necessarily constant, as shown in FIGS. 40B and 41B, but instead will vary in conformance with the shape of the device and the geometry of the vasculature during use. Furthermore, it is understood that the ultrasound wavelength may also be a function of the transmission wire diameter, such that even for constant diameter sections, the wavelength of the standing wave may vary if the cross-sectional shape of one section is different from that of a second section. For example, the transmission wire can be a substantially exponential, catenary, straight, quadratically, or hyperbolically tapered cross-sectional dimension, or a uniform cross-sectional dimension, or combinations thereof With further reference to FIGS. 40B and 41B, it will be understood that the means of coupling the proximal end of the horn to an ultrasound energy source, the operating mode (i.e. resonance or anti-resonance), as well as the transmission characteristics of the ultrasound source itself (i.e. the structure of the transducer assembly) will all determine the exact location of the leading displacement maximum 342. Thus, it is important to note that this invention should not be construed to be limited by deviations of the leading displacement maximum 342 from the location shown in FIGS. 40B and 411B. That is, displacement maximum 342 is shown in FIGS. 40B and 41B for illustrative purposes only. The exact location of displacement maximum )42 has no bearing on the positioning of displacement nodes and anti-nodes of the standing wave pattern relative to the step-transitions and other structures taught in this invention.

It is to be further understood that the standing wave pattern that develops within the probe, and which is partially depicted in FIGS. 40B and 411B, is a function of the tortuosity of the probe during use. That is, the geometric configuration of the blood vessels within which the probe is inserted, will determine to a greater or lesser extent, the exact operating frequency and exact location of the nodes and anti-nodes of the standing wave at any given moment as the probe is advanced or retracted within the vessels. In practice, the dimensions of the probe and the operating frequency of the probe are selected so that the desired nodal positions of the standing wave, as taught herein, are achieved for a selected range of geometries. In this way, the nodal positions in the probe will be ideal at certain locations within the target vessel and will deviate minimally from ideal at other locations. Thus, it is to be understood that references herein to the positioning of the displacement nodes and anti-nodes of the standing wave pattern relative to the step transitions and other structures taught herein relate to the preferred or ideal or average positions, around which some variation will naturally occur as the probe is manipulated through a given vessel tortuosity. For this reason, references herein to standing wave positions are designated "approximate," or "average."

In the event the transmission member tapers, such as medium 350 of FIG. 41A, then a distal end 351 of the tapered portion preferably is located at a displacement maximum 352. This tapered section then functions as a half-wavelength horn, the amplification properties of which are well understood. Thus, if a proximal end 353 is at a displacement maximum 417, the distal terminus of the taper 351 should be located at a distance equal to an integral multiple of $\lambda/2$. For illustrative purposes, in FIG. 41B, terminus 351 is shown located at $3\lambda/2$. The tapered section may be followed by a constant diameter section with a distal step down 355 which should be at a displacement minimum 356.

Referring again to FIG. 1, in accordance with preferred embodiments of the invention, to section A, if it includes a taper, preferably has a tapered length equal to an integral multiple of half wavelengths of the intended frequency of operation. At the terminus of section A, there may be a transition zone B, which is a step transition to section C, wherein section C has diameter $C_i < A_f$. To effect maximum displacement amplification, step-transition zone B is preferably placed at or near a displacement node (i.e., a displacement minimum). Thus, if section A includes a tapered section which is an integral multiple of half-wavelengths, it should be followed by a straight section of a length equal to an odd multiple (i.e. 1, 3, 5 . . . ) of quarter-wavelengths. In this way, section A begins at the proximal end 129 at a displacement maximum, and ends at its distal end 130 at a displacement minimum (displacement node). If section A is straight (i.e., has a constant diameter as is shown in FIG. 40A), then it should begin at a displacement maximum and terminate at a displacement node.

Device 100 also includes a mass 150 at the distal tip thereof. Mass 150 is designed and shaped to distribute ultrasound energy and/or perform work in accordance with the application of interest.

Ultrasound device 100 (as well as other probes discussed herein) is understood to operate in a resonant (or anti-resonant) mode; i.e., it supports a standing wave (preferably a longitudinal wave) when energized by ultrasonic stimulation at proximal end 129. Consequently, it is preferred that mass 150 is located at a displacement maximum (anti-node). Transition zone D may be located at a displacement node or anti-node. For example, transition zone D may involve a joint that couples several parallel lengths of transmission media, of diameter $E_i$, to section C. In that case, it may be determined that the mechanical strength of transition zone D is insufficient to support maximum stress. For such a case, transition zone D may be located at or near a displacement maximum, as the displacement maximum corresponds with a location having minimal stress (stress node).

It is understood that the techniques for assembling the sections of this invention are equally applicable to systems that promote or focus ultrasound energy to enhance the absorption of drugs, induce apoptosis in cells, and/or treat tissue, tumors, obstructions, and the like, within and without the body, and for systems to be utilized in laproscopic surgery, for ultrasonic scalpels, and to induce tissue hyperthermia for cancer radiation therapy, for example.

Furthermore, it will be understood that while several examples given herein refer to intravascular applications of the invention employing guide catheters, introducer sheaths, guidewires, and the like, the invention is equally applicable to topical or superficial treatments, therapies administered in cavities of the body, intramuscular and intra-tissue treatments, including the application of ultrasound to fatty deposits to assist in their removal, the use of ultrasound to enhance healing, or to stimulate or suppress the functioning of bodily organs.

An ultrasound probe constructed in accordance with a second embodiment of the invention is shown generally as ultrasound probe 200 in FIG. 2. Probe 200 is similar in construction to probe 100, except that sections B, C, and D of probe 200 are further subdivided to provide for additional step downs in cross-sectional area. Thus, tapered section A, which is preferably machined from a single piece of metal, such as aluminum, can be reduced in length. This can significantly reduce the cost of probe 200, compared to probe 100. Tapered section A of probe 100 or 200 may be formed with any combinations of constant diameter and reducing sections, or a single section of diameter $A_i$.

Probe 200 includes n sections ($C_1$ to $C_n$) each of constant diameter, separated by n transition zones $B_1$ to $B_n$, where preferably diameter $C_i < A_f$ and $C_{i+1} < C_i$ for i=1 to n. Each of transition zones B or $B_1$ to $B_n$ may be abrupt or tapered, and sections A and C, or any of $C_1$ to $C_n$ may be formed from one material or from a multitude of materials, such as aluminum or titanium. Thus, constant diameter sections C or $C_i$ may be formed separately (as, for example, from drawn wire) and then joined at zones B or $B_i$ to sections A, D, E and F. Alternatively, constant diameter sections C or $C_i$ may be formed as an integral unit such as from a single wire which may be ground to conform to the aforementioned criteria. Accordingly, sections A, B and C or sections A, B, C and D may be formed from an integral unit as from a single rod, for example, which may be machined to conform to the aforementioned design criteria. In the event probes 100 or 200 are formed from multiple sub-components which are joined at zone B (or $B_i$), D and F, the connections should be free of voids and provide for the intimate contact of the joined members. The materials for each subsection may be carefully selected to maximize performance of the device by satisfying the specific requirements of the device along its length. Specifically, the physical requirements of the device may change along its length as for example, certain subsections may require greater flexibility and other subsections greater strength, while others may require greater erosion resistance and so on.

In the event probes 100 or 200 are formed from multiple sub-components which are joined at zone B (or $B_i$), D and F, the connections may be achieved by a variety of methods, including, but not limited to, welding, adhesive bonding, swaging, crimping, clamping, screwing, or pinning. In addition, one or several of those connections may be fashioned to be releasable, thus permitting the interchange of components during or between procedures. For example, section A of probes 100 or 200 may be rendered reusable, resterilizable or modifiable by the interchange or addition of alternative sections C (or $C_i$). Similarly, section 25 of FIG. 3 may be rendered reusable, resterilizable, or modifiable by the interchange or addition of alternative transmission members 40 and tip 50.

It is also noted that any or all of the surfaces may be coated with a moisture barrier or hermetic coating to extend longevity by reducing stress corrosion.

Mass 150 can be in the shape of a sphere, a cylinder or a grooved cylinder. It can be ground or otherwise patterned, textured with holes or notches, and so forth to promote or focus ultrasound emissions, promote surface cavitation or promote selected flow patterns. The shapes disclosed in U.S. Pat. No. 5,269,297, the content of which is incorporated by reference, are suitable.

Mass 150 may be formed directly as an integral portion of section E or mass 150 may be formed separately and then attached to section E. For example, mass 150 may be formed as a welded or brazed mass at the distal end of section E and then further machined, if desired, to impart additional surface texture or structure to mass 150. Alternatively, mass 150 may be formed or machined separately and then attached to section E by a variety of methods including but not limited to welding, adhesive bonding, swaging, crimping, clamping, screwing or pinning.

Mass 150 may be formed from a wide variety of materials which may be selected based upon the requirements of the specific application. For example, mass 150 may be constructed from any one or several of metals, ceramics, cermets, glass or polymers. Mass 150 may be molded or otherwise formed directly onto section E of FIG. 1 or FIG. 2.

To dissipate energy lost as heat and/or to damp unwanted vibrational modes, a probe in accordance with the invention may be bathed with a coolant. The coolant may be directed over and around the probe, for example, by incorporating a sheath around some or all sections of the probe. The sheathing can be affixed to the probe at one or more of the displacement nodes of the standing wave, but preferably at any of the displacement nodes of section A, which are proximal of transition B. Additional sheathing may be incorporated for providing a passageway for a guidewire or other auxiliary tool which may serve to steer the device to, or position the device at, its intended location.

The coolant pathway may be used additionally or alternatively as a conduit for the delivery or withdrawal of other fluids, or bodily tissue matter, or gels or suspensions or the like. For example, the sheathing may serve as a pathway to administer therapeutic drugs, or the sheathing may serve as a conduit for the withdrawal of ablated material. Furthermore, drugs, such as streptokinase, urokinase, and platelet inhibitors, and contrast media, and other fluids whose function or efficacy would be enhanced by ultrasound or that would enhance the application of ultrasound at the treatment site, may be infused within the coolant fluid for cooling the ultrasound probe or delivered through a separate passageway within or without the ultrasound probe to the treatment site.

Referring to FIG. 3, a probe with a constant diameter section as part of the horn section is shown generally as probe 20. A horn 25, having a tapered section T and a first constant diameter section S is constructed to be coupled to an ultrasound energy source. Probe 20 also includes a transmission member 40 coupled to horn 25 at transition zone B', and a tip 50 coupled to the distal end of transmission member 40. Ultrasound energy sources disclosed in U.S. Pat. No. 5,269,297, the content of which is incorporated by reference, are suitable.

Horn 25 includes a proximal end 29, a distal end 30, a tapered section 26 of reducing diameter from proximal end 29 to a transition point 28 and a straight section 27 with a constant diameter from transition point 28 to distal end 30. Horn 25 is preferably machined or turned down from a single piece of metal, preferably aluminum 7075. Horn 25 transitions from tapered section 26 to straight section 27 at transition point 28, which should be located approximately at a displacement anti-node. The length of section 26 is approximately a multiple of $\lambda/2$, where $\lambda/2$ is the half wavelength of the standing wave, measured from anti-node to anti-node. The frequency of the ultrasonic energy generated by the ultrasonic energy source used to excite the device into resonance is designated f. In a preferred embodiment of the invention, f ranges from 10 to 100 kHz, more preferably about 42 kHz. It is to be understood that the selected frequency of operation of the device may be an overtone, i.e., the operating frequency is not necessary the fundamental resonant (or anti-resonant) frequency of the device. Horn 25 is preferably 7075 aluminum and the length of tapered section T is 144 mm long. In said preferred embodiment, the diameter of the proximal end of horn 25 is 12.7 mm, which tapers to a 1.0 mm diameter at horn transition point 28. While horn 25 is preferably tapered, in alternate embodiments, it may have a constant diameter.

In a preferred embodiment of the invention, the diameter of straight section 27 remains a constant 1.0 mm from transition point 28 to horn distal end 30. Distal end 30 is connected to transmission member 40 at transition zone B' and includes at least one transmission wire 45, having a wire proximal end 46 and a wire distal end 47. Horn distal end 30 may be connected to transmission wire proximal end 46 by a number of coupling devices and techniques which are known in the art and otherwise, such as welding, including laser, diffusion, and thermal welding, adhesive bonding, swaging, crimping, clamping, screwing, pinning, or with a mechanical connector. The joint should be free of voids and provide for the intimate contact of the joined members.

Transmission member 40 also includes a highly flexible Section E', which is shown in FIG. 3 as being formed with three wires 60 of fine diameter, coupled to wire 45 at a 1-to-3 coupling joint 55 at transition zone D'. While Section E' preferably consists of three wires, in this embodiment, at least two wires are advantageous to give the device extra flexibility and high power transmission. Coupling 55 includes one opening at its proximal end for insertion of distal end 47 of wire 45 and three openings in its distal end for the proximal ends of the three fine wires 60. At least ends of wires 60 are advantageously knurled prior to inserting wires 60 within openings of coupling 55. Wires 60 may be glued or otherwise coupled to coupling 55 using techniques known in the art, such as welding, adhesive bonding, swaging, crimping, clamping, screwing, pinning or with a mechanical connector.

Transition zone D' can also be designed as a single step amplification wherein Section E' 10 consists of a single wire having a diameter less than wire 45. In a preferred embodiment of the invention, wires 45 and 60 are composed of high strength titanium wire.

Figure 31:
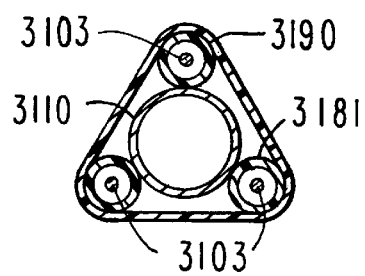
FIG. 31 is a cross-sectional view taken along line 31—31 of FIG. 30.

A bullet-shaped tip 50 is coupled to the three fine wires 60 by means of three openings in the proximal end of tip 50. In a preferred embodiment, the three openings in coupling 55 and in tip 50 are spaced so as to form an equilateral triangle, concentric about the central longitudinal axis of coupling 55 and tip 50, as is shown in FIG. 31.

Tip 50 is provided with a notch 51 to improve cavitation as is shown in FIG. 14. It will be understood that displacement amplitudes that exceed a threshold level particular to a given fluid type may be used to induce cavitation in that fluid. Cavitation bubbles in a sound field may be used advantageously to concentrate energy and enhance ablation or other desired effects. Tip 50 may also be provided with proximal chamfers 52, as shown in FIG. 14. Tip 50 may also be provided with proximal chamfers 52, as shown in FIG. 14 to aid in the retraction of the probe following a procedure. A radiopaque marker may be affixed to tip 50. The radiopaque band may be affixed to the proximal or distal end of tip 50, and may be contained within a recess or affixed to the outside of the tip. Alternatively, tip 50 may be fashioned from a radiopaque material or it may be coated with a radiopaque film. In a preferred embodiment, a pocket or recess 53 in the distal end of tip 50 is fashioned, as shown in FIG. 14, wherein a radiopaque marker band is affixed with adhesive.

Tip 50 may also be provided with an opening for a guidewire, and a guidewire sheath may be installed in the opening and extend proximally from the distal end. In a preferred embodiment, the guidewire opening is centrally located in tip 50, passing along its longitudinal axis. Fine wires 60 may be separately sheathed, and said sheathing may extend between tip 50 and coupling joint 55. Wire 45 may also be sheathed and said sheathing may be connected to the separate sheathing of wires 60 and may extend proximally to a coolant port to allow coolant to be injected to bathe all or part of sections 26, 27 and 40.

Figure 42A:
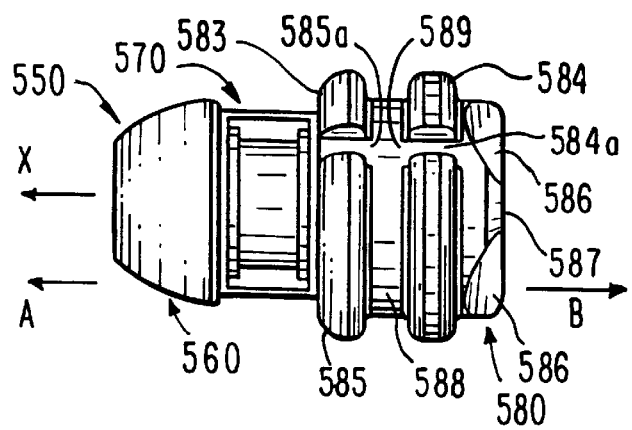
Figure 42C:
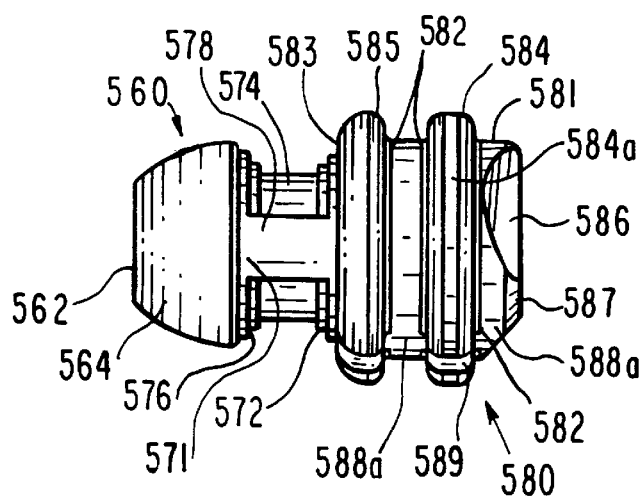
FIG. 42C is a side view of the distal tip of FIG. 42A rotated 90 degrees about a longitudinal axis.
Figure 42B:
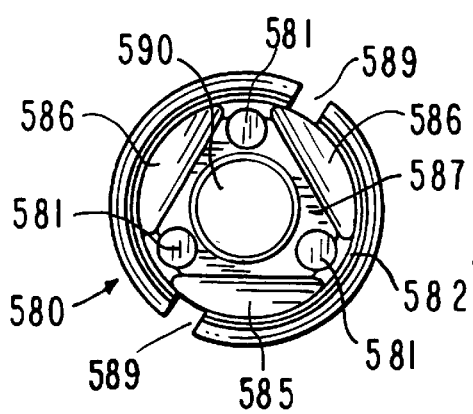

In another embodiment of the invention, tip 550 is shown generally in FIGS. 42A–42C. Tip 550 includes a distal section 560, an intermediate section 570, and a proximal section 580. As with tip 50 depicted in FIG. 3, proximal section 580 of tip 550 is shaped to accept three wires of a multi-wire section. As is shown in FIG. 42C, proximal section 580 includes bores 581 sized and shaped to accept wires 60. In a preferred embodiment, at least the ends of wires 60 are knurled prior to inserting wires 60 into bores 581 and proximal section 580 is crimped to secure wires 60 within bores 581. Wires 60 may also be glued or otherwise coupled to tip 550 using other techniques known in the art, such as welding, adhesive bonding, swaging, crimping, clamping, screwing, pinning or with a mechanical connector.

Tip 550 includes a central bore 590, which extends through proximal section 580, intermediate section 570 and distal section 560, and is sized to accommodate a guide wire (not shown). In a preferred embodiment, that portion of central bore 590 contained within distal section 560 may include a counterbore 591 to provide a space for a radiopaque marker (not shown), which may be affixed within counter bore 591 with an adhesive or any other affixation means known in the art, including, but not limited to, those described above in connection with affixing wires 60 to tip 50.

As is shown best in FIGS. 42A and 42C, proximal section 580 includes a substantially cylindrical body 581 having a rear face 587, a surface 588a and a distal wall 583. Proximal section 580 includes a first ring 584 and a second ring 585 spaced apart from first ring 584 in a longitudinal direction depicted in FIG. 42A as arrow X. First ring 584 preferably includes a flattened surface 584, however, first ring 584 may have any cross-sectional shape including a rectangular, a square or an arcuate shape, for example. The walls of first and second rings 584 and 585 are preferably substantially perpendicular to surface 588a of body 581 to facilitate the creation of low pressure zones, when activated within a vessel, as is described in more detail below.

First ring 584 and second ring 585 extend from body 581 and can optionally be formed, as is shown in FIGS. 42A and 42B, with discontinuities 584a and 585a, respectively, that permit movement of the fluid medium in which tip 550 operates or an occlusion along surface 588a and through discontinuities 584a and 585a. Optionally, discontinuities 584a and 585a are located on the same radial plane thereby forming a channel or gap 589. First ring 584 and second ring 585 advantageously have at least two sets of discontinuities 584a and 585a equally spaced apart radially.

Channel 589 is advantageously formed substantially perpendicular to first ring 584 and second ring 585. Channel 589, however, can have any orientation in relation to the longitudinal axis X, including, as is described below, a spiral or oblique orientation, and can have a variety of widths. The width of channel 589 may vary.

Proximal section 580 includes beveled surfaces or flats 586, which extend from rear face 587 distally toward first ring 584, thereby creating a truncated rear face 587. Proximal section 580 also includes fillets 582, which are preferably located at the base of first ring 584 and second ring 585 where rings 584 and 585 meet surface 588a of body 581. As is discussed in more detail below, flats 586 and fillets 582 serve as surfaces at which cavitation bubbles can form when tip 550 is activated to move in the direction indicated by arrow A in FIG. 42A.

Intermediate section 570 optionally includes proximal steps 572, which step down from second ring 585 to a step landing 574, and distal steps 576 which step up from step landing 574 to distal section 560. Proximal steps 572 and distal steps 576 can include one or more increases in diameter as measured from step landing 574. Preferably, proximal steps 572 and distal steps 576 form substantially vertical surfaces where cavitation bubbles can form in low pressure areas during oscillation of tip 550. Steps 572 and 576 in connection with step landing 574 form a radial channel having a first width at the level of step landing 574 and at least a second width formed at a fixed distance measured radially from step landing 574. Intermediate section 570 optionally also includes lands 578, which extend from the top-most step of proximal steps 572 to the top-most step of distal steps 576, and which serve to support intermediate section 570. Lands 578 along with the surface of the top-most steps of steps 572 and 576 form an intermediate upper surface 571.

Distal section 560 is preferably substantially hemispheroidal or paraboloidal in shape with the nose of distal section 560 truncated by a plane substantially perpendicular to the longitudinal axis X. Distal section 560 includes a distal face 562 and an outer surface 564. As with proximal section 580, distal section 560 may include channels (not shown), which are preferably substantially parallel with the longitudinal axis X, to promote the movement of an occlusion from face 562 of tip 550 to intermediate section 570, where the occlusion can be lysed by combination of cavitation and fluid agitation Thus, tip 550 preferably consists of a narrow intermediate section 570, which is sandwiched by sections with comparatively larger diameters, proximal section 580 and distal section 560. In a preferred embodiment, distal section 560 has a maximum diameter that is less than the maximum diameter of proximal section 580. Most preferably, distal section 560 is approximately 1.6 mm in diameter at its maximum diameter, and proximal portion 580 is approximately 2.2 mm in diameter at its maximum diameter.

As described above, tip 550 is constructed to induce cavitation in the blood contained within a blood vessel, for example. Because probe 100 is constructed to move the tip at high speeds in a direction parallel to the longitudinal axis of probe 100, it can be advantageous to form surfaces substantially perpendicular to the direction of motion so as to create or enhance cavitation. In this way, it is believed that cavitation bubbles form in low pressure areas where such surfaces create low pressure areas during oscillation. Thus, when tip 550 moves in a direction parallel to the longitudinal axis, depicted as arrow A in FIG. 42A, low pressure areas form that lead to the formation of cavitation bubbles near the substantially perpendicular walls of distal steps 576. Similarly, when tip 550 moves in a direction parallel to the longitudinal axis, depicted by arrow B, low pressure areas form that lead to the formation of cavitation bubbles near the substantially perpendicular walls of proximal steps 572.

Lysing fields are also believed to be formed at proximal section 580 and distal section 560, where areas of low pressure are believed to be formed when tip 550 oscillates in a longitudinal direction. Lysing fields of proximal section 580 are formed at flats 586 and fillets 582 while lysing field of the distal section 560 is formed at distal face 562. Thus, when tip 550 is moved forward longitudinally in the direction shown by arrow A, cavitation is believed to be promoted in the areas near distal steps 576, flats 586 and fillets 582. And, when tip 550 oscillates in the direction depicted by arrow B, cavitation is believed to be promoted near proximal steps 572 and distal surface 562. Such phenomena have been observed in several in vitro and in vivo experiments.

In a preferred embodiment, tip 550 is approximately 0.124 inches in length as measured in the longitudinal direction, and the proximal dimensioned as follows: distal section 560 measures approximately 0.033 inches in length and has a maximum diameter of 0.065 inches, intermediate section 570 measures approximately 0.032 inches in length and has a minimum diameter of 0.046 inches, and proximal section 580 measures approximately 0.059 inches in length and has a maximum diameter of 0.069 inches; steps 572 and 576 measure approximately 0.003 inches in length and range from 0.046 to 0.065 in diameter; rings 584 and 585 measure approximately 0.015 inches in length and have a maximum diameter of 0.087 inches; bore 590 is approximately 0.033 inches in diameter and counterbore 591 is approximately 0.035 inches in diameter.

Thus, when the occlusion is located forward of distal surface 562, and tip 550 is energized and moved toward contact with the occlusion, the occlusion can be channeled over distal section 560 toward distal steps 576 and proximal steps 572 to what may be termed "lysing fields," where a combination of cavitation and fluid agitation pulls and breaks the occlusion into its constituent parts. The hemispheroidal shape of distal section 560 promotes the flow of portions of the occlusion over outer surface 564 of distal section 560 and toward distal wall 583 of proximal section 580. The differences in diameters between proximal section 580, intermediate section 570 and distal section 560 can also help create vortices that help pull the occlusion apart and direct the occlusion into the lysing fields created near distal steps 576 and proximal steps 572.

To promote the formation of cavitation bubbles, preferably all or part of the surface of tip 550, including outer surface 564, can be roughened to provide imperfections. Also, those surfaces designed to create lysing fields may be roughened or treated with a coating to enhance the formation of cavitation bubbles.

FIGS. 43–50 depict tips constructed in accordance with further embodiments of the invention. Such further embodiments include tips having different combinations of elements designed to, among other benefits, facilitate the formation of cavitation bubbles, the agitation of the fluid medium and thrombus contained therein, and the movement of the occlusion proximally from the distal most portion of the tip along the length of the tip. It is to be understood by those skilled in the art that the elements depicted herein can be combined differently to achieve similar or enhanced effects.

Figure 43B:
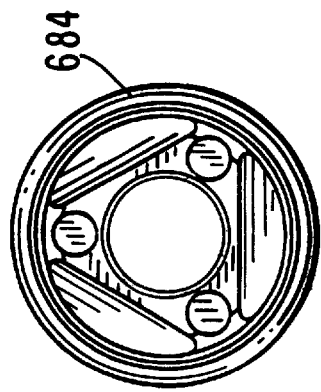
Figure 43A:
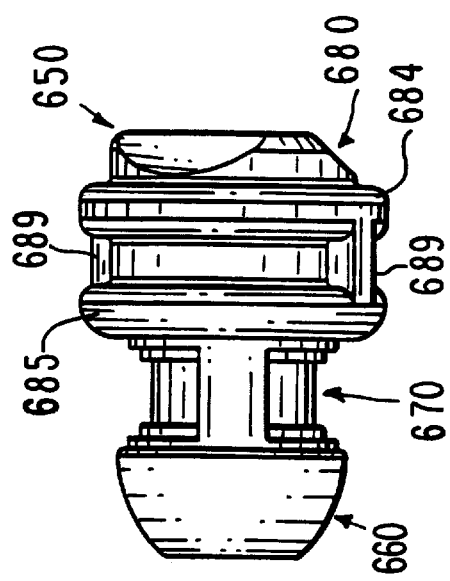

Turning to FIGS. 43A and 43B, a tip 650 formed in accordance with the invention is shown having a proximal section 680, an intermediate section 670, and a distal section 660. Tip 650 differs from tip 550 in that rather than having channels 589 formed substantially perpendicular to first ring 584 and second ring 585, tip 650 includes lands 689 that bridge first ring 684 and second ring 685 in the longitudinal direction to support proximal section 680 and promote agitation of the fluid medium and the occlusive material that moves near distal section 680 when tip 650 is actuated. Lands 689 need not be oriented parallel to the longitudinal axis of tip 650. For example, lands 689 may bridge first ring 684 and second ring 685 at any orientation, including an oblique orientation.

Figure 44B:
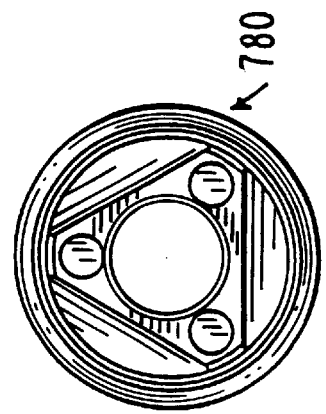
Figure 44A:
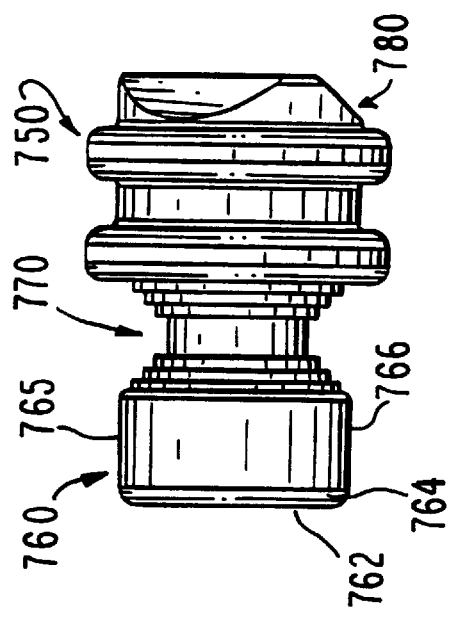

Turning to FIGS. 44A and 44B, there is depicted a tip 750 constructed in accordance with another embodiment of the invention, having a proximal section 780, an intermediate section 770, and a distal section 760. Tip 750 differs from tip 550 in that distal section 760 is formed with a more cylindrical shape, having a substantially flat nose 762 and sides 765 and 766. As a result, rather than having a generally hemispheric or bullet shape as is depicted in FIG. 42B, distal section 760 has a constant outer diameter, except at the rounded edges 764. Therefore, tip 750 is depicted as a parallelogram when viewed from the side. It is understood, however, that sides 765 and 766 need not be parallel to the longitudinal axis of tip 750. Sides 765 and 766 can have an arcuate or an oblique orientation. When the orientation is oblique, sides 765 and 766 would thereby create a trapezoidal cross section when viewed from the side. Thus, the shape of distal section 760 when viewed from the side may be any shape, including rectangular, thromboidal or trapezoidal, by way of non-limiting example.

FIGS. 45A and 45B depicts a tip 850 constructed in accordance with yet another embodiment of the invention. Tip 850 includes a distal section 860, an intermediate section 870 and a proximal section 880. Proximal section 880 includes a rear face 887 and flats 886, which extend from rear surface 887 distally toward intermediate section 870. Distal section 880 also includes a body 881, a rear outer surface 889 and steps 885, which are formed on body 881. In this manner, the diameter of distal section 880 increases from rear outer surface 889 to body 881.

Intermediate section 870 includes proximal steps 872, distal steps 876 and a step landing 874 located intermediate proximal steps 872 and distal steps 876. From body 881, the outer diameter of tip 850 decreases through a series of proximal steps 872 to step landing 874. Thereafter, the outer diameter of tip 850 increases through a series of distal steps 876 to a surface 864 of distal section 860. As is shown in FIG. 45A, proximal steps 872 may be of greater number than distal steps 876. Further, proximal steps 872 and distal steps 876 may be formed as a spiral, as is shown in embodiments described below, such that the diameter of tip 850 decreases or increases at a defined rate when measured at a point within proximal steps 872 or distal steps 876.

FIGS. 46A and 46B depict another embodiment of a distal tip 950 constructed in accordance with the invention, having a proximal section 980, an intermediate section 970, and a distal section 960. Proximal section 980 includes a body 981 having channels 989 that spiral or corkscrew obliquely through a portion of body 981. Further, intermediate section 970 includes distal steps 974a, 974b and 974c, each having different heights, and proximal steps 972a, 972b and 972c, each having different heights. Distal steps 974a and 974b and proximal steps 972a and 972b are substantially perpendicular to the longitudinal axis of tip 950, while distal steps 974c and proximal steps 972c are preferably the same width as distal steps 974a and 974b, and proximal steps 972a and 972b, respectively.

Figure 47A:
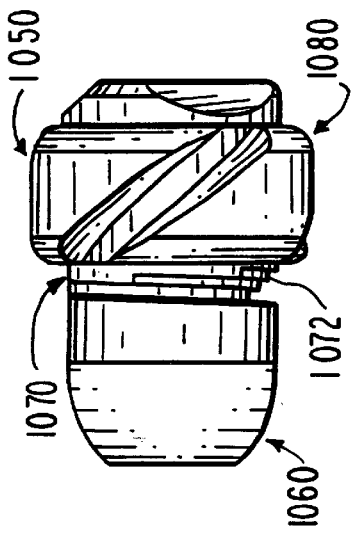
Figure 47B:
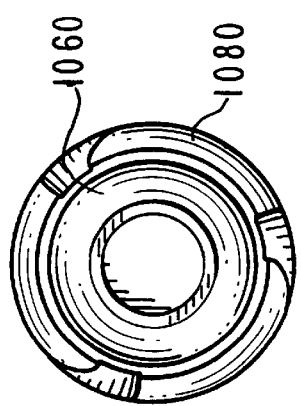

FIGS. 47A and 47B depict another embodiment of a distal tip 1050 constructed in accordance with the invention, having a proximal section 1080, an intermediate section 1070, and a distal section 1060. Intermediate section 1070 is eccentric in its construction in that on one side of intermediate section 1070 includes proximal steps 1072 that step down from proximal section 1080, while on the opposite side, the diameter surface of intermediate section 1070 is on the same plane as the surface of distal section 1060. In this way, when tip 1050 oscillates in the longitudinal direction, the tip vibrates eccentrically causing further agitation to the fluid medium and occlusion.

Figure 48A:
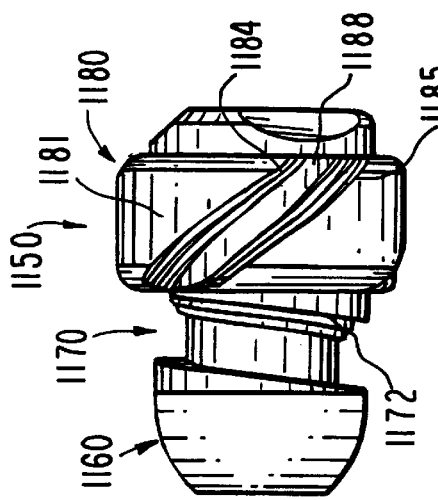
Figure 48B:
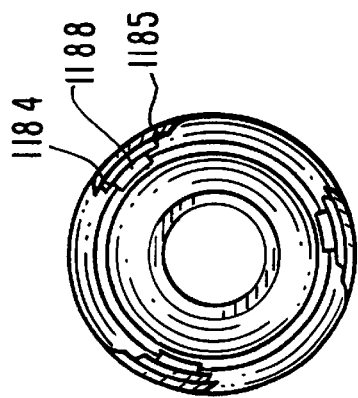

FIGS. 48A and 48B depict another embodiment of a distal tip 1150 constructed in accordance with the invention, having a proximal section 1180, an intermediate section 1170, and a distal section 1160. Proximal section 1180 includes a body 1181 having a channel 1188 and a series of steps 1184 that step down in diameter from body 1181 to channel 1188 and a series of steps 1185 that step up from channel 1188 to body 1181. These series of steps 1184 and 1185 and channel 1188 are formed as spirals in body 1181 and are oblique in orientation as compared with the longitudinal axis X. Steps 1184 and 1185 and channel 1188 may be a curved or straight in orientation. Intermediate section 1170 includes steps 1172, which are also curved spiral steps whose orientation is preferably opposed to the orientation of steps 1184 and 1185 of the proximal section 1180. The walls of steps 1172, 1184 or 1185 need not be perpendicular to the surface from which they extend. In fact, in a preferred embodiment, the walls may extend obliquely from the surface as is clearly shown in FIG. 48B. Steps 1184, 1185 and channel 1188 are constructed to promote agitation and longitudinal twisting of the fluid medium to facilitate agitation and dissolution of the occlusion.

Figure 49A:
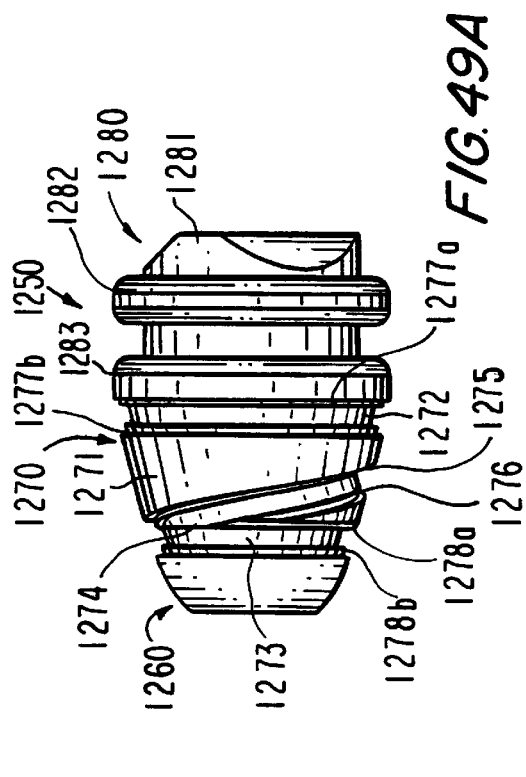
Figure 49B:
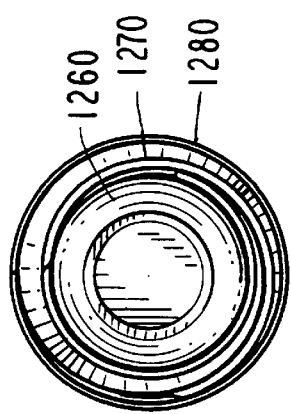

FIGS. 49A and 49B depict another embodiment of a distal tip 1250 constructed in accordance with the invention, having a proximal section 1280, an intermediate section 1270, and a distal section 1260. Proximal section 1280 includes a first ring 1282 and a second ring 1283 formed on body 1281. In this embodiment, intermediate section 1270 has a diameter greater than that of distal section 1260, but is less than the diameter of ring 1283 of proximal section 1280. Intermediate section 1270 includes a body 1271 having a first channel 1272 and a second channel 1273 formed substantially perpendicular to the longitudinal axis of tip 1250, and a third channel 1273 formed in body 1271 and having a spiral orientation. Intermediate section 1270 also includes steps 1275, which step down from body 1271 to third channel 1274 and steps 1276 which step up from channel 1274 to body 1271. Intermediate section 1270 also includes step 1277a and step 1277b, which respectfully step down from ring 1283 to channel 1272 and step up from channel 1272 to body 1271, and step 1278a and step 1278b which respectfully step down from body 1271 to channel 1273 and step up from channel 1273 to distal section 1260.

Figure 50A:
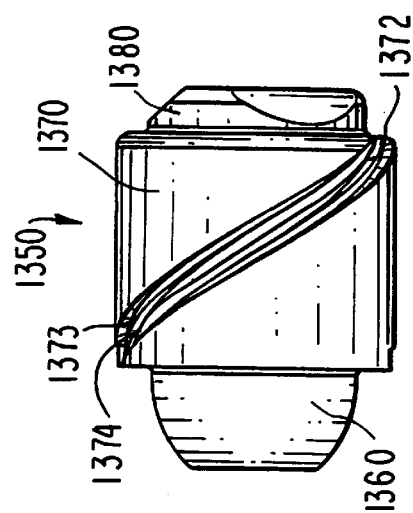
Figure 50B:
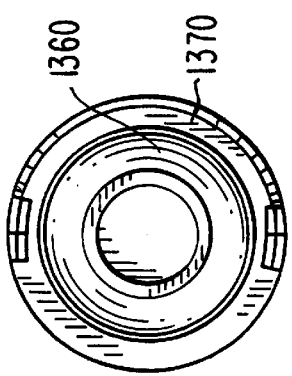

FIGS. 50A and 50B depict another embodiment of a distal tip 1350 constructed in accordance with the invention, having a proximal section 1380, and an intermediate section 1370 and a distal section 1360. In this embodiment, distal section 1360 and proximal section 1380 are simplified, and the diameter of intermediate section 1370 is greater than both the diameters of proximal section 1380 and distal section 1360. As with prior embodiments, intermediate section 1370 includes a channel 1372 having steps 1373 and 1374.

FIG. 51 depicts another embodiment of a distal tip 1390 constructed in accordance with the invention, having a proximal section 1391, an intermediate section 1392 and a distal section 1393. The primary difference of this embodiment is that distal section 1392 has channels 1395 spaced apart radially that extend substantially parallel to the longitudinal axis. Alternatively, channels 1395 can be oblique in orientation as compared with the longitudinal axis X.

Referring to FIGS. 4A, 4B, 4C and 5, another preferred embodiment of the invention is exemplified by horn 525, which includes a straight section 527 of constant diameter and a transition section in the form of a joint 535 in the distal end thereof. Joint 535 is bored to accept a transmission wire. This embodiment may include a region of increasing diameter 529 prior to joint 535 (see FIG. 4B), so that the diameter of joint 535 is slightly greater than the diameter of straight section 527 to provide greater strength at joint 535 between a horn distal end 530 and a transmission wire (not shown). In one example of such an embodiment, a horn 525 has a straight section 527 with a diameter of 1 mm which increases to 1.09 mm at the distal end of the region of increasing diameter 529.

In one preferred embodiment, joint 535 has a bore diameter of approximately 0.63 mm, and a bore depth of approximately 5 mm, and is mechanically crimped onto a transmission wire, which is preferably formed of titanium and preferably has a diameter of approximately 0.62 mm. To further increase the strength of the crimp joint, in accordance with a preferred embodiment of the invention, the surface of the proximal 4 mm of the transmission wire may be roughened prior to crimping.

In an alternative embodiment joint 535 is replaced with joint 735 shown in FIG. 7B, which does not include a region of increasing diameter.

It is important to note that the placement of a stepped-down reduction in diameter from horn 525 to a transmission wire at or near a displacement node offers the maximum displacement amplification. Despite this fact, the prior art generally teaches away from using step downs in this fashion because of the high level of stress associated with such a transition. However, this shortcoming of the prior art is overcome by introducing a high strength joint and the ability to combine different and appropriate materials at the joint. Also, by locating the joint approximately at a displacement node, energy transfer can be made more efficient.

Because an ultrasound transmission device must be sized to accommodate different treatment sites that have varying distances between the point of entry of the probe into the patient's body and the point within the body to be treated, it is understood that other embodiments will require different lengths and diameters than the preferred coronary embodiments. Variations in length are still described by the general formulation described in FIGS. 1, 2 and 3.

Referring to FIGS. 8 through 13, a variety of probe designs which satisfy the principles of construction taught herein are shown. These variations employ step transitions with joints constructed according to the advantages taught herein, though details of those connections, such as that of FIG. 4B or connecting member 55 of FIG. 3, are not shown. It is to be understood that neither the diameters nor the lengths of the sub-components in these or any of the other figures contained herein are to scale, nor are any of the proportions to be construed as representative or limiting. In FIG. 8, three consecutive step transitions (801, 802 and 803) are shown, each of which may be located at a displacement node. The first step transition is shown with a radiused transition, which may be applied similarly to any of the step transitions taught herein, to effect a strain relief.

Figure 10:
Figure 11:
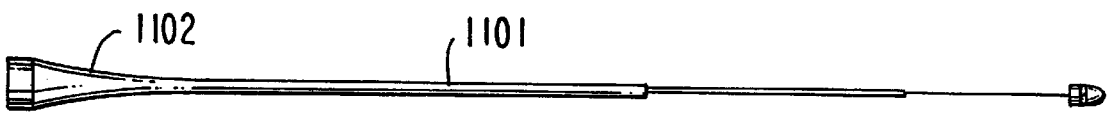
Figure 12:
Figure 13:
Figure 13A:

FIG. 9 is similar to FIG. 8 except that all transitions (901, 902 and 903) are shown as abrupt steps. FIG. 10 employs a proximal, tapered horn section 1001. FIG. 11 employs an elongated straight section 1101 which is integral with a proximal horn section 1102. FIG. 12 shows the use of two parallel wires 1201a and 1201b in the distal-most transmission wire section for enhanced flexibility of this section. The use of two or more wires in the distal section permits the passage of a guidewire along the central longitudinal axis of the distal tip. FIG. 13 is similar to FIG. 12, except that the distal two-wire section is replaced with a three-wire (1301a, 1301b and 1301c) section. In FIG. 13A, the proximal section is shown to consist of two consecutive half-wavelength horns followed by an integral straight section which terminates at a displacement node at transition point B.

Referring again to FIG. 3, in one preferred embodiment of the invention designed for coronary blood vessels, the ultrasound horn, 526, includes a proximal tapered section T, formed with a length of 144 mm and an initial diameter of 12.7 mm that tapers to a diameter of 1 mm at transition point 28. The horn then extends distally, over section S for a distance of 567 mm at this constant diameter, and terminates at distal end 30. The horn is connected by means of joint 735 of FIG. 7B to transmission wire 45 which has a length of 544 mm. The distal end of transmission wire 45 is connected to distal three-wire section E' via connector 55. Section E' has a wire length of 160 mm and is connected to tip 50. In another modification of a preferred coronary embodiment, joint 735 is replaced with joint 535 of FIG. 4B. In another modification of a preferred coronary embodiment, section S is extended to a total length of 847 mm and transmission wire 45 has a length of 264 mm. In another modification of a preferred coronary embodiment, section T has a total length of 233 mm.

Referring again to FIG. 3, in one preferred embodiment designed for peripheral vessels, such as AV shunt vessels, ultrasound horn 525 includes a proximal tapered section T formed with a length of 144 mm and an initial diameter of 12.7 mm that tapers to a diameter of 1 mm at transition point 28. The horn then extends distally, over section S for a distance of 173 mm at a constant diameter, and terminates at distal end 30. The horn is connected by means of joint 735 of FIG. 7B to transmission wire 45, which has a length of 30 mm. The distal end of transmission wire 45 is connected to distal single wire section E' via connector 55. Section E' has a wire length of 227 mm and is connected to tip 50. In another modification of the above-preferred peripheral embodiment, joint 735 is replaced with joint 535 of FIG. 4B. In another modification of the above-preferred peripheral embodiment, transmission wire 45 has a length of 89 mm and section E' is constructed as a two- or three-wire section with a length of 160 mm. In another modification of the above-preferred peripheral embodiment, transmission wire 45 has a length of 544 mm and Section E' is constructed as a two- or three-wire section with a length of 160 mm.

As discussed above, transmission member 40 of FIG. 3 may include one or more transmission wires, each having constant diameters, and each successive transmission wire having a smaller diameter. The successive wires may be formed as an integral unit by machining each diameter down from a single rod of material or they may also be formed separately and then joined.

Referring again to FIG. 3, in a preferred embodiment of the invention, distal end 47 of transmission wire 45 is joined with a multi-wire section 60, which in a preferred embodiment, includes three titanium wires. The diameter of transmission wire 45 range between 1.0 mm and 0.2 mm, while the diameter of fine wires 60 can range between 0.5 mm and 0.01 mm. The length of transmission wire 45 can range between 0 mm and 1000 mm, while the length of fine wires 60 can range between 0 mm and 300 mm. In a preferred embodiment, transmission wire 45 has a diameter of approximately 0.62 mm, and a length of approximately 544 mm, and the wires of the multi-wire section 60 have a constant diameter of approximately 0.29 mm, and a length of approximately 160 mm. While in this example, junction 55 of transmission wire 45 and fine wires 60 is located near a displacement maximum, junction 55 may be located at any position along the standing wave.

In a preferred embodiment, coupling 55 is fabricated from high strength aluminum (preferably aluminum 6061) and includes a high strength crimp connection to transmission wire 45 and aerospace-grade epoxy connections to fine wires 60. In this example, the bore diameter for the crimp connection is approximately 0.63 mm with a depth of 3 mm, and the bore diameter for the fine wire adhesive connections is approximately 0.31 mm with a depth of approximately 1.5 mm.

In another preferred embodiment of the invention, the proximal end of horn 29 of FIG. 3, and proximal end 29' of FIG. 4A can include a threaded bore having a diameter of one-quarter inch and 12 mm deep for receiving the distal tip of an ultrasound source. In other embodiments, connection between the ultrasound source and the horn can be made via bayonet-type twist connections, spring-loaded snap connections, and a variety of other quick-connections. Referring to FIGS. 6A and 6B, a keyed O-ring groove 600 is utilized as a means of both establishing a fluid seal between the proximal end of sheathing 155 of FIG. 14 and horn 525 and preventing any relative twisting of sheathing 155 and horn 525. O-ring groove 600 is preferably located at a displacement node (i.e. a displacement minimum) so as to avoid damping of the transmitted energy by the O-ring groove. In one embodiment, O-ring groove 600 is located at a distance of 83 mm from the proximal end of the first transmission member. Preferably, ring 601 may extend 0.25 mm from the surface of the horn and have a thickness of 0.5 mm. A hex ring 602 may extend 0.5 mm from the surface of the horn, have a thickness of 0.8 mm, and have a diameter between flat surfaces of 3.7 mm, and a diameter between opposite apex points of 4.2 mm. It will be evident to those of ordinary skill in the art that an ultrasound transmission device constructed in accordance with the invention, including the foregoing examples, can readily fit within and be delivered to a thrombus in a coronary artery through a 7 French guide catheter.

Referring again to FIG. 3, tip 50 is connected to the distal end of at least one transmission wire 60. Preferably, tip 50 is shaped to accept three wires of a multi-wire section, and is positioned at a displacement maximum such that it will oscillate maximally in a longitudinal direction. In a preferred embodiment, tip 50 is formed of aluminum, preferably 6061 aluminum and is 1.65 mm in diameter. Alternatively, tip 50 may be formed of a titanium alloy such as Ti6Al/4V, which can serve to strengthen tip 50 and eliminates the need for a distal marker band, as the vanadium within the alloy makes the tip 50 visible under an angiogram.

To dissipate energy lost as heat and/or to dampen unwanted vibrational modes, the device may be bathed with a coolant. The coolant may be directed over and around the device by affixing a thin flexible sheathing, preferably formed of polyimide, or other high strength, thin walled, low friction material around some or all sections of the device. The sheathing is preferably affixed to the device at one or several displacement nodes. Additional sheathing may be applied to the device to provide a passageway for a guidewire or other auxiliary tool that may serve to steer the ultrasonic probe to its intended location.

In another preferred embodiment, all or some surfaces of the horn and/or transmission wires are coated with a moisture barrier or hermetic coating, such as parylene, to extend the longevity of those sections by reducing or eliminating stress corrosion.

Referring to FIGS. 6A and 14, a sheathing 155 of one or more sections can be disposed around horn 525 and extend distally to just beyond a coupling member 1455. The sheathings can be reduced in diameter as the diameter of the transmission medium decreases. An advantageous sheathing material is polyimide, in view of its ability to be formed into extremely thin diameters, its strength and its low friction.

Referring to FIG. 14, a single transmission wire 1445 of relatively large diameter is joined to three wires 1403 of relatively small diameter, including wires 1401 and 1402, shown, and a third wire, not shown, but positioned behind wires 1401 and 1402. Wire coupling 55 is constructed to have a proximal single hole to receive wire 1455, and three distal holes to receive wires 1403. In a preferred embodiment, the three wires 1403 and their receiving holes in coupling 55 are spaced equally in a circular pattern to form an equilateral triangle, concentric with the central longitudinal axis of coupling 55.

In a preferred embodiment, coupling 55 is mechanically crimped onto single transmission wire 1445. To further increase the strength of the crimp joint, in accordance with a preferred embodiment of the invention, the distal surface of transmission wire 1445 may be roughened prior to crimping. In a preferred embodiment, coupling 55 is bonded to fine wires 1403 using a high-strength, aerospace-grade epoxy. Alternative means of attaching coupling 55 may also be employed as previously taught herein.

Sheathing 155 may be disposed about horn 525, single transmission wire 1445, wire coupling 55, and extend distally to beyond the proximal end of coupling member 1455. Sheathings 1481 and 1482 are disposed around wires 1401 and 1402, respectively, and the third wire is sheathed similarly. A distal end 155a of sheathing 155 overlaps a portion of coupling 1455, and is attached to coupling 1455 with adhesive. Sheathing coupling 1455 is constructed to have three through-holes positioned and sized to receive the sheathings that are disposed around wires 1403. The sheathings disposed around wires 1403 are attached to coupling 1455 with adhesive. Coupling 1455 and the sheathings disposed around wires 1403 may be separate members joined as described above, or they may be formed of a single member, as a single length of extruded multi-lumen tubing. It is to be understood that other embodiments of wire and sheathing arrangements are encompassed by this invention including designs that use more or fewer than three wires 1403, and their associated sheathings. In one embodiment, fluid, such as saline solution, flows through sheathing 155, through coupling 1455, and out through the distal ends of the wire sheathings disposed about wires 1403.

If the ultrasonic probe design includes a multi-wire distal section, as shown for example in FIG. 14, then it is important that sheathing 155 be prevented from rotating relative to the central ultrasound transmission member 1445 and coupling 55. In such a case, if relative motion were permitted, transmission wires 1403 could become twisted just proximal of coupling 1455, and failure of one or more of the transmission wires could be accelerated. To prevent this, O-ring groove 600, which is located at a displacement node, may be shaped or keyed (see FIG. 6A). A similarly shaped receiving pocket is then fashioned in the sheathing structure, such that once engaged with the horn, the sheathing cannot be rotated relative to the horn. It is understood that for those embodiments where the transmission members always lie on the central axis of the probe, for example, in FIG. 14, if wires 1403 are replaced with a single centrally located wire or, for example, in FIGS. 8–11, such "keying" is not necessary. However, the location of an O-ring groove or similar sealing mechanism to establish a fluid pathway between the sheathing and the horn (or transmission members) should be at a displacement node whether keying is used or not.

In another preferred embodiment, as shown in FIG. 14, the sheathing of wires 1403 terminates proximal to a cavitation tip 1450, to create an expansion gap 1480 between the sheathing and tip 1450. Expansion gap 1480 is typically a few millimeters in length, and thus provides adequate spacing to allow the sheathings disposed around wires 1403 and sheathing 155 to expand or contract during use, without effecting interference with cavitation tip 1450. The expansion and contraction of such sheathing is a consequence of normal elongation and compression of the polymeric sheathing material when the probe is energized and manipulated during a procedure.

FIG. 14 also shows a guidewire tube 1430 to facilitate the positioning of probe tip 1450 at the desired location. In the construction shown in FIG. 14, guidewire tube 1430 is of a similar diameter as the sheathing of wires 1403, and extends from a location 10 to 15 centimeters proximal cavitation tip 1450 into and through tip 1450. Tube 1430 can include a flared distal tip to provide a safety retention feature, in the event that tip 1450 breaks when the probe is energized, such as at a notch 1451. Tube 1430 is held in place by bands 1490, which are wrapped around the sheathing of wires 1403. Bands 1490 are shown in end cross-section in FIG. 31 as 3190, and again in FIG. 30 as 3190.

In another preferred embodiment of the invention, a cavitation tip 1550 is fitted with a safety insert 1501, 1601, 1701, 1801, or 1901 as shown in FIGS. 15–19, respectively. Guidewire tube 1430 of FIG. 14 is denoted as tube 1510, 1610, 1710, 1810, and 1910 in FIGS. 15–19, respectively. Safety inserts 1501,. 1601, 1701, 1801, and 1901 serve to retain sections of tip 1550, such as the radiopaque marker or a fractured front end of tip 1550, in the event that dislocation occurs during use. The safety inserts also serve to separate the cavitation tip 1550 from a guidewire which may be inserted inside the safety insert. The safety insert is preferably tightly connected to, or locked onto, tip 1550 in such a manner as to eliminate or minimize differential movement between the safety insert and tip 1550.

A variety of methods of attachment of the safety insert to tip 1550 may be employed depending upon the materials of construction selected for the particular application. Attachment methods include, but are not limited to, adhesive bonding, crimping, molding, melt-bonding, swaging, flaring, screwing, pinning or coating. In addition, the safety insert and tip may be fashioned as a single component using a single material, as for the case where the selected material serves the multiple functions of applying ultrasound to the treatment site, resisting abrasion by the guidewire, and providing safety retention of fractured components.

It is advantageous to decouple the safety insert from the probe sheathing, which, as noted above, will tend to expand and contract during use as the probe is energized and manipulated during a procedure. Decoupling prevents chafing or abrasion of the sheathing by the cavitation tip. Preferred embodiments of the associated decoupling mechanisms are shown in FIGS. 15 to 35. It is understood that while retaining flares are drawn in FIGS. 15 to 19 as a way of affixing the safety insert to the cavitation tip, other affixment arrangements as depicted in FIGS. 20 to 28 will serve as well, including adhesive and melt bonding.

Figure 15:
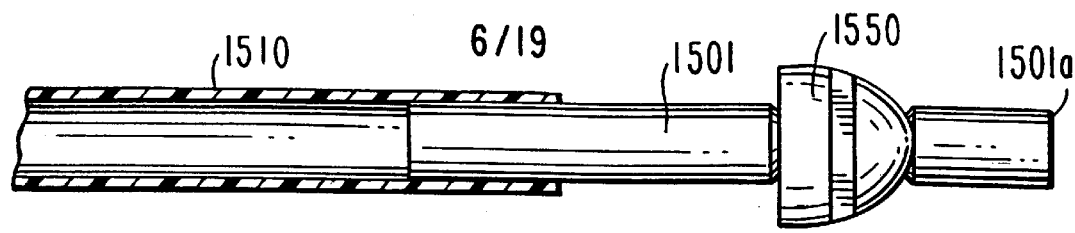
FIGS. 15–27, and 29 are side views of variations of the distal tip section of ultrasound transmission devices constructed in accordance with embodiments of the invention with the energy transmission wires not shown.

FIG. 15 shows a guidewire tube 1510 terminating just proximal tip 1550. Safety insert 1501 is positioned within and in a slidable piston-in-cylinder fit with tube 1510. It is preferable that insert 1501 fit inside tube 1510 and not vice versa to avoid creating a point at which the guidewire would be impeded when it is threaded from distal end 1501a of insert 1501 towards the proximal end of the probe.

FIGS. 16–29 and 52 show additional embodiments of the invention including different safety inserts. Safety inserts are preferably formed of abrasion-resistant materials. An insert may optionally be included in the cavitation tip. In still other embodiments, a gap may exist proximal of the safety tip and in still other embodiments, the guidewire tube can terminate proximal of the cavitation tip and the guidewire can pass through the cavitation tip without a guidewire tube or safety insert therebetween.

Figure 16:
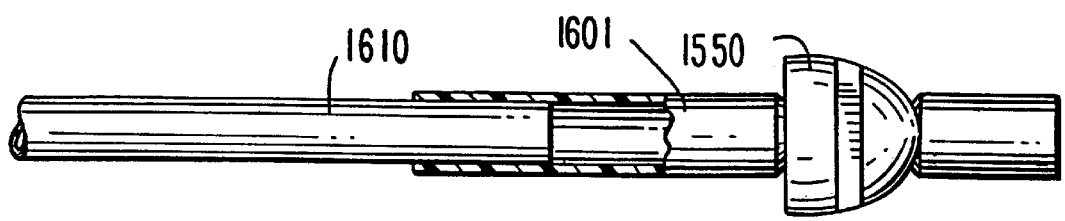

Referring to FIG. 16, a safety insert 1601 is shown slidably disposed over the distal end of a guidewire tube 1610. Though preferably, guidewire tube 1610 or the proximal diameter of insert 1601 can be sized so that guidewire tube 1610 fits over insert 1601, as in FIG. 15.

Figure 17:
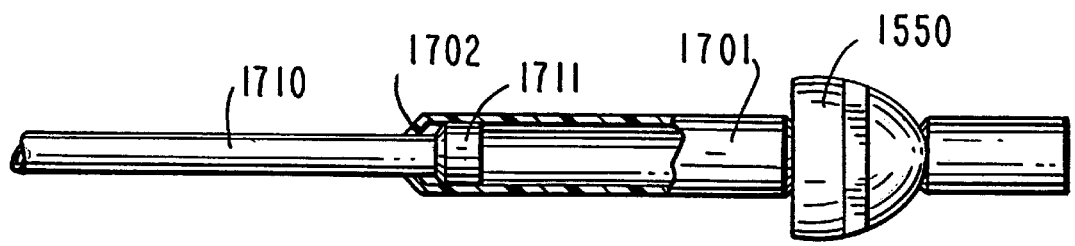

Referring to FIG. 17, an insert 1701 is shown slidably disposed over the distal end of a guidewire tube 1710 similar to the construction of FIG. 16. However, a flare 1711 is formed in the distal end of tube 1710 and a constriction 1702 is formed in the proximal end of insert 1701. In this manner, tube 1701 and tube 1710 are mutually captive.

Figure 18:
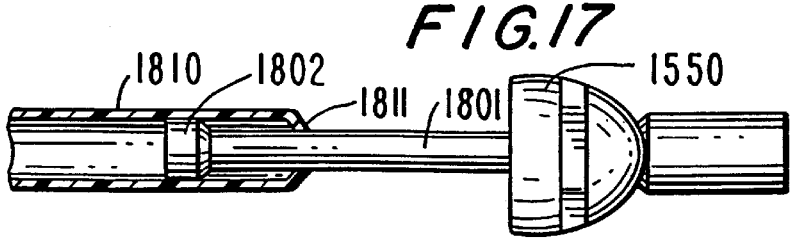

Referring to FIG. 18, an insert 1801 is shown slidably disposed in a distal end of a guidewire tube 1810, similar to the construction of FIG. 15. However, a constriction 1811 is formed in the distal end of tube 1810, and a flare 1802 is formed in the proximal end of insert 1801. Thus, tube 1801 and tube 1810 are mutually captive.

Figure 19:
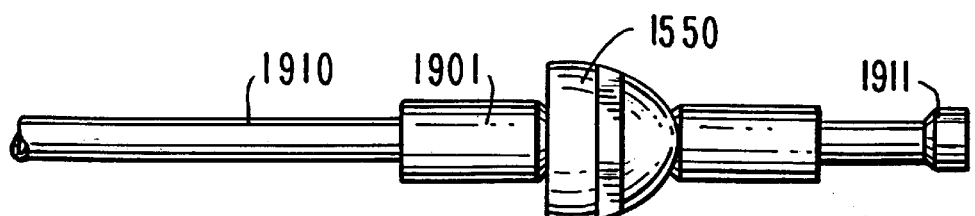

Referring to FIG. 19, an insert 1901 is shown slidably disposed over the distal portion of a guidewire tube 1910. The guidewire tube 1910 passes through insert 1901. Tube 1910 may project distally through 1901 and may be fitted with a safety flare 1911. Safety flare 1911 serves to capture tube 1901 or tip 1550 in the event of release.

Figure 20:
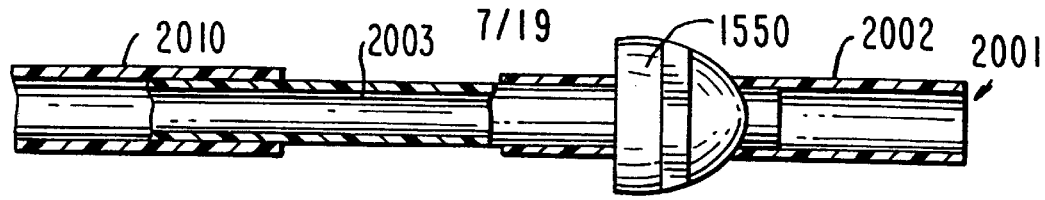

Referring to FIG. 20, an insert 2001 is shown slidably disposed inside guidewire tube 2010. Insert 2001 consists of two sections, tube 2002 and tube 2003, which are joined together and attached to tip 1550. Tube 2002 fits over tube 2003.

Figure 21:
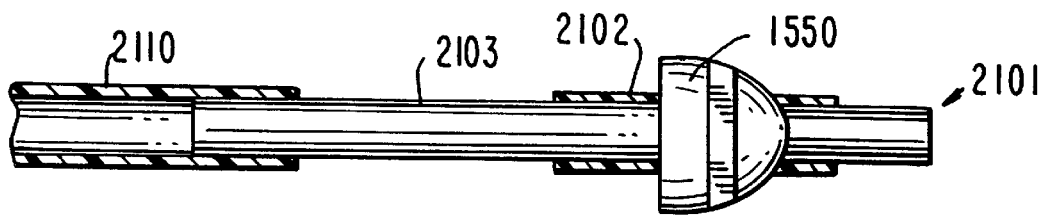

Referring to FIG. 21, an insert 2101 is shown sidably disposed inside guidewire tube 2110. Insert 2101 consists of two sections tube 2102 which fits over tube 2103, and which are joined together and attached to tip 1550.

Figure 22:
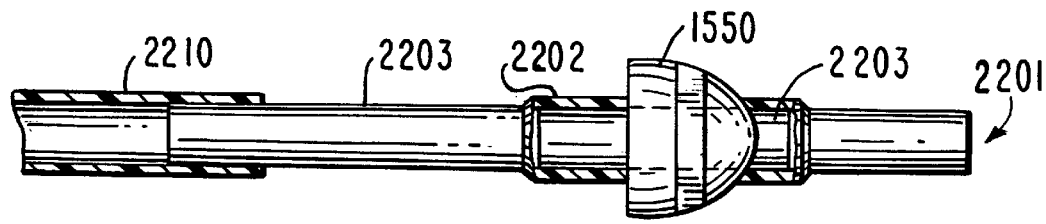

Referring to FIG. 22, an insert 2201, is shown slidably disposed inside guidewire tube 2210. Insert 2201 consists of two sections, tube 2203 and tube 2202, which fits over tube 2203, which are joined together and attached to tip 1550.

Figure 23:
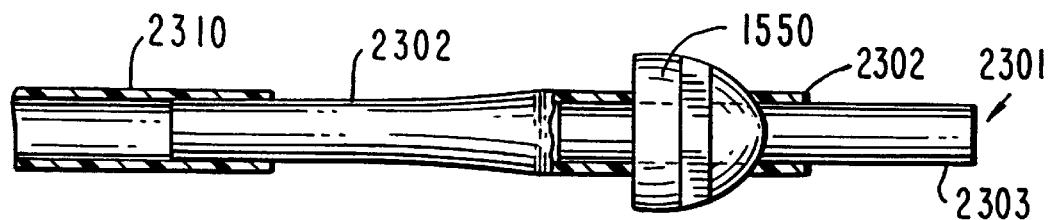

Referring to FIG. 23, an insert 2301 is shown slidably disposed inside a guidewire tube 2310. Insert 2301 consists of two sections, a tube 2302 which fits over a tube 2303, and which are joined together and attached to tip 1550.

Figure 24:
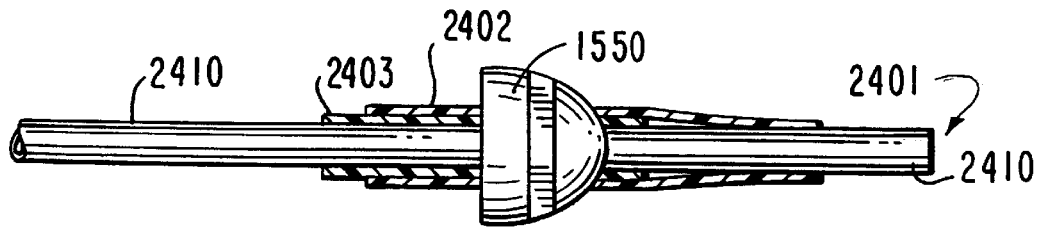

Referring to FIG. 24, an insert 2401 is shown slideably disposed over a guidewire tube 2410. Insert 2401 consists of two sections, a tube 2402, which fits over a tube 2403, which are both joined together and attached to tip 1550.

Figure 25:
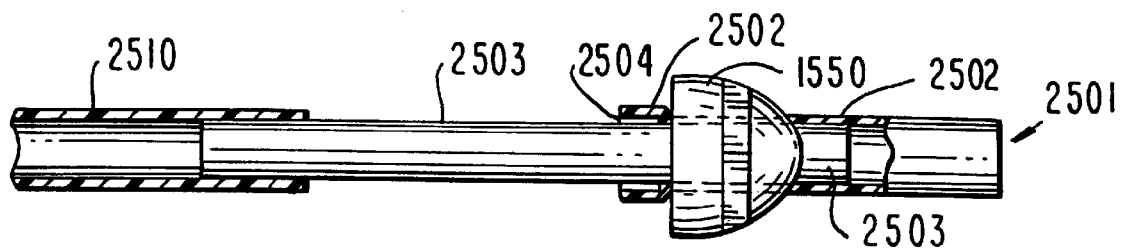

Referring to FIG. 25, an insert 2501 is shown slidably disposed inside a guidewire tube 2510. Insert 2501 consists of three sections, a tube 2502 which fits over a tube 2503 and over a proximal safety stop 2504. All three sections are joined together and attached to tip 1550.

Figure 26:
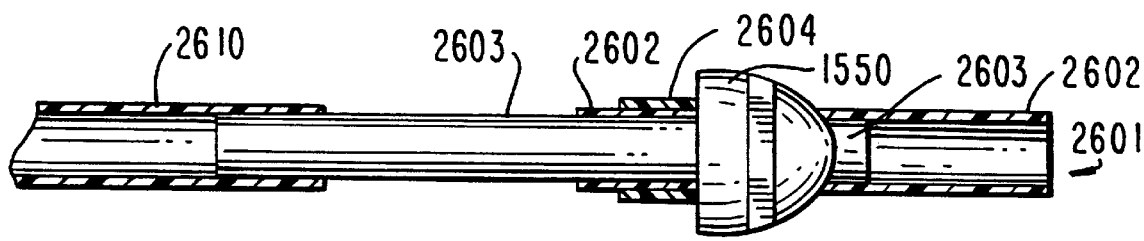

Referring to FIG. 26, a guidewire tube 2610 is shown in a piston arrangement with an insert 2601, which is disposed through tip 1550. Insert 2601 consists of three sections: a proximal safety stop 2604, a tube 2603, and a tube 2602, which fits over tube 2603, and inside proximal safety stop 2604, all of which are joined together and attached to tip 1550.

Figure 27:
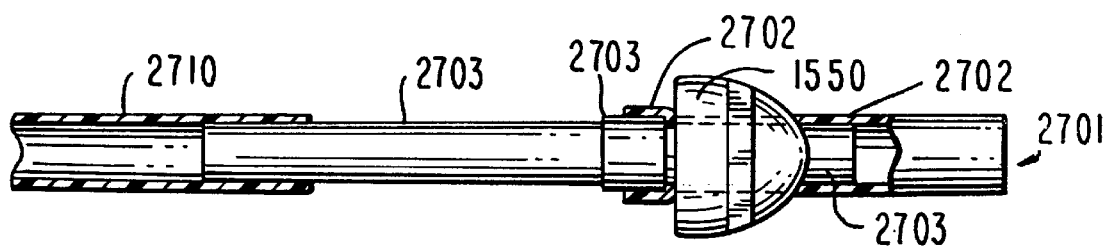

Referring to FIG. 27, an insert 2701 is shown slidably disposed inside a guidewire tube 2710. Insert 2701 consists of two sections, a tube 2702 which fits over a tube 2703. Tube 2703 is shown with an enlargement which serves as the proximal safety stop. Tubes 2702 and 2703 are joined together and attached to tip 1550.

Figure 28:
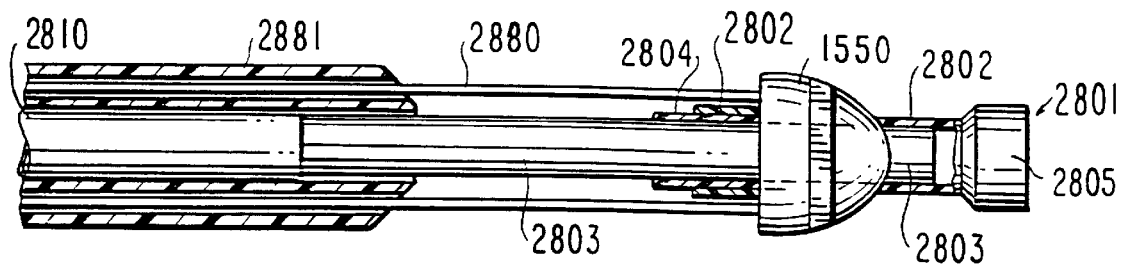
FIGS. 28 and 30 are side views of variations of the distal tip section of ultrasound transmission devices constructed in accordance with embodiments of the invention.

Referring to FIG. 28, an insert 2801, which is similar to the assembly of FIG. 25, is shown incorporated in a multi-wire distal assembly, including three titanium wires 2880 (two shown), and their respective sheathings 2881. Insert 2801 is shown slidably disposed inside a guidewire tube 2810. Insert 2801 consists of three sections, a tube 2802 which fits over a tube 2803 and over a proximal safety stop 2804 all three sections are joined together and attached to tip 1550. Insert 2801 is shown with a distal safety flare 2805. It is to be understood that distal safety flares may be added to any of the insert designs disclosed herein.

Figure 29:
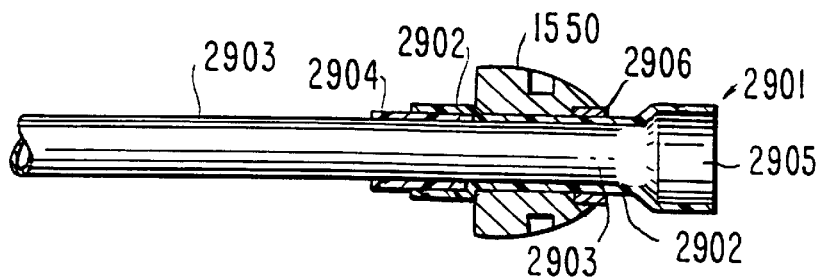

FIG. 29 is a sectional view of an insert similar to that of FIG. 28. Insert 2901 consists of three sections, a tube 2902 which fits over a tube 2903 and over a proximal safety stop 2904. All three sections are joined together and attached to tip 1550. Insert 2901 is shown with a distal safety flare 2905. FIG. 29 also shows a tip 1550 in which a radiopaque marker 2906 is affixed therein.

Figure 52:
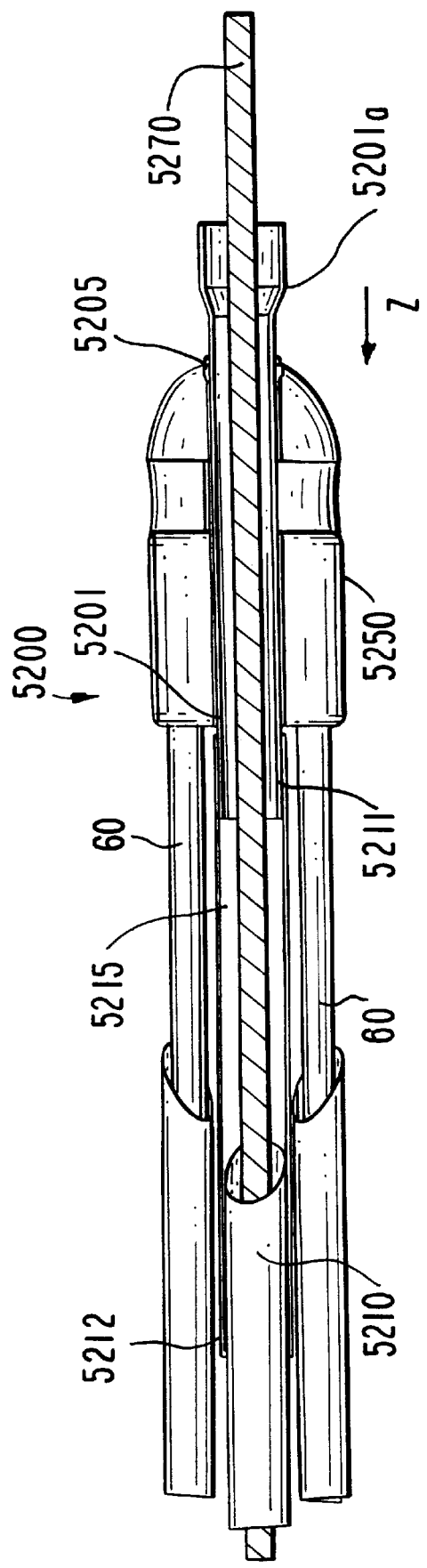
FIG. 52 is a side view of a distal tip section of the ultrasound transmission device constructed in accordance with embodiments of the invention.

FIG. 52 depicts a sectional view of a distal tip section 5200 like that of FIG. 15. Distal tip section 5200 includes of a guidewire 5270, a tip 5250 having a bore 5205 sized to accommodate guidewire 5270, a first tube 5201 having a first diameter sized to fit within bore 5205 and a flared portion 5201a having a second diameter that is greater than the diameter of bore 5205. In this way, first tube 5201 is prevented from moving in a proximal direction Z. First tube 5201 is preferably formed using Hytrel or another art-known material, such as a plastic or polymer.

Distal tip section 5200 also includes a guidewire tube 5210 terminating just proximal tip 1550, and a piston tube 5215 having a free end 5212 and a fixed end 5211 connected to first tube 5201. Guidewire tube 5210 is positioned within and in a slidable piston-in-cylinder fit with piston tube 5215. It is preferable that guidewire tube 5210 fit inside piston tube 5215 to avoid creating a point at which the guidewire would be impeded when it is threaded from flared portion 5201a of first tube 5201 toward the proximal end of the probe. In this way the first tube 5201 can be decoupled from guidewire tube 5210, while guidewire 5270 is advantageously shielded from contacting wires 60 and causing damage thereto.

First tube 5201 is preferably glued or heat-bonded to free end 5212 of piston tube 5215, but can be connected using any techniques known in the art. Preferably, piston tube 5215 is formed of polyimide, has an inside diameter of 0.020 inches, and a length that is approximately 0.35 inches, but in any event is sized to permit guidewire tube 5210 to expand during sonication.

Referring to FIG. 31, a partial view of a sheathing bundling arrangement is shown. A tube 3110 corresponds to tube 2810 of FIG. 28. A plurality of sheathings 3181 correspond to sheathings 2881 of FIG. 28, and band 3190 corresponds to band 1490 of FIG. 14. A corresponding band may be applied to the assembly of FIG. 28. Tubes 3110 and 3181, and band 3190 are understood to be mutually attached. Sheathings 3181 are shown to fit loosely about fine wires 3103. The distal portion of guidewire tube 3110 is positioned between sheathings 3181, coaxial with the central axis of the device, and band 3190 is wrapped about sheathing 3181 of fine wires 3103. Thus the distal portion of tube 3110 is positioned to accept a slidably disposed safety insert; for example, insert 2801.

Figure 30:
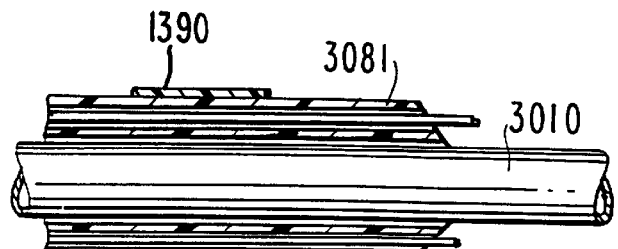

Referring to FIG. 30, guidewire tube 3010 is shown to project beyond sheathings 3081. Such an arrangement may be employed to accept a slidably disposed safety insert of the types shown in FIGS. 16, 19 and 24.

Figure 32:
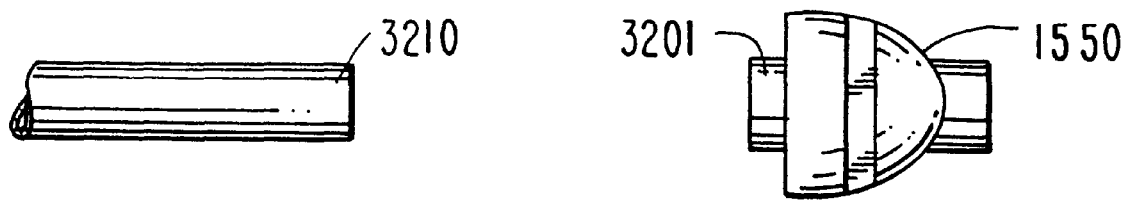
FIGS. 32–39 are side views of additional embodiments of the distal tip section of an ultrasound transmission device constructed in accordance with embodiments of the invention.
Figure 33:
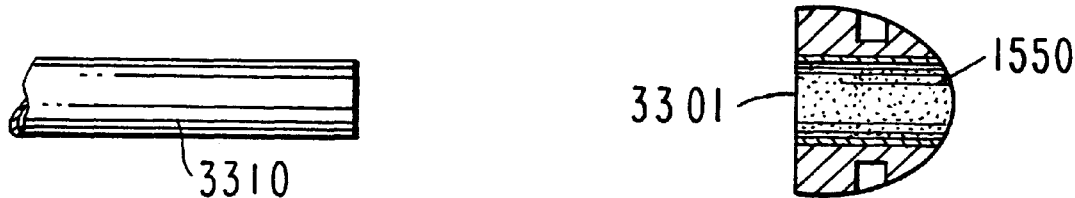

Referring to FIG. 32, a distal tip assembly is shown in which an insert 3201 is shown spaced apart from the distal end of a guidewire tube 3210. In FIG. 33, insert 3201 is replaced with a polymeric coating 3301. In still another embodiment, polymeric coating 3301 and insert 3201 can be omitted.

Figure 34:
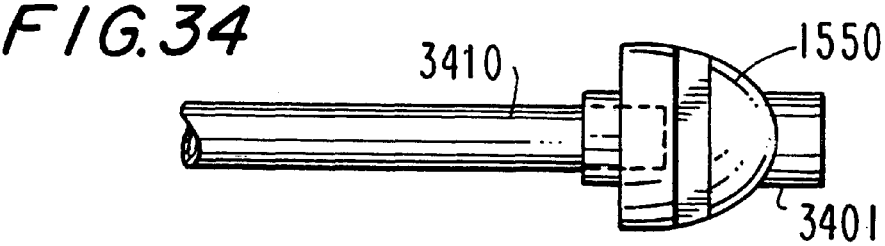
Figure 35:
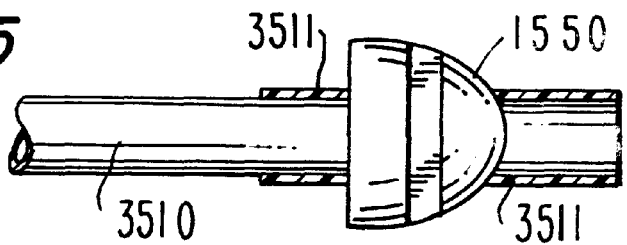
Figure 36:
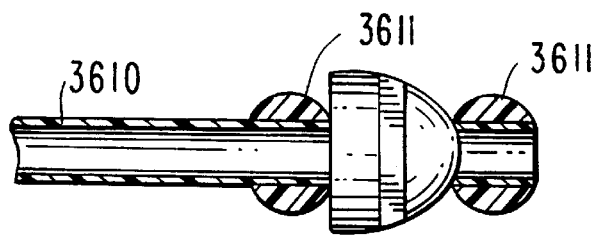

Referring to FIG. 34, a construction similar to that of FIG. 19 is shown, except that the distal end of a guidewire tube 3410 which is slideably disposed relative to insert 3401 terminates inside insert 3401. In FIG. 35, a pair of insert retention sleeves 3511 are shown attached to tube 3502. In FIG. 36, sleeves 3511 are replaced by insert retention bulbs 3611.

Figure 37:
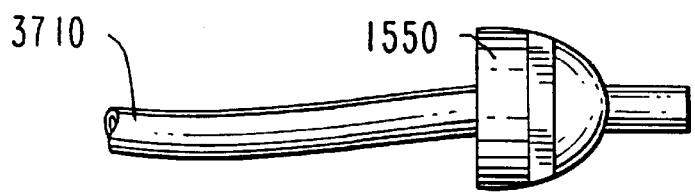

Referring to FIG. 37, a guidewire tube 3710 is shown slideably disposed through tip 1550. In order to provide enhanced abrasion resistance, tube 3710 may be formed of abrasion resistant polymer such as polyethylene, nylon, polyester, polyurethane and polypropylene.

Figure 38:
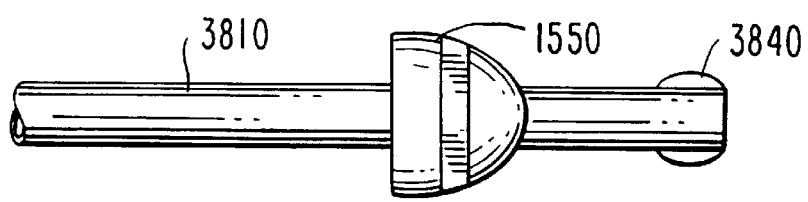

Referring to FIG. 38, a construction similar to that of FIG. 37 is shown, except that wireguide tube 3710 is replaced with tube 3810 having a safety flare or bulb 3811 at its distal end, to help retain a broken distal portion of tip 1550, in the event tip 1550 fails.

Figure 39:
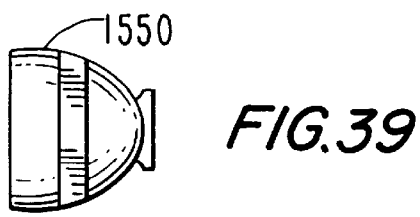

FIG. 39 shows a tip 1550 in which a radiopaque marker or the cavitation tip itself may be flared to reduce the abrasive surface contact between tip 1550 and a guidewire or safety insert configurations shown herein.

The following example of a therapeutic ultrasound method for the ablation of an occluding thrombus in a human's coronary blood vessel is provided for purposes of illustrating features and aspects of the invention and is not intended to be construed in a limiting sense.

Prior to undergoing the ablation procedure, a human patient is treated with intracoronary nitroglycerine (200 mg), aspirin (250–325 mg chewable or intravenous) and intravenous heparin (15.000 units), to obtain an Activated Clotting Time of greater than 300 throughout the procedure. First an introducer sheath is used to establish a point of entry into the body. Through the introducer sheath, a relatively stiff wire is introduced, over which a guiding catheter is advanced to the area proximal the lesion. In one embodiment of the invention, the guide catheter is advanced to the ostium of the coronary artery. Then a guidewire is advanced through the guide catheter and through the lesion. Next, an ultrasound transmission device in accordance with the invention is loaded onto the guidewire (not shown) and advanced through the guide catheter until the tip of the device is positioned in close proximity to the occlusion within the blood vessel. Alternatively, the ultrasound probe can be loaded onto the guidewire and both advanced together through the guide catheter. Preferably, the tip includes a radiopaque marker that permits the physician to locate the tip accurately, using fluoroscopy.

The tip is then positioned in close contact with the occlusion, preferably about 1 to 2 mm beyond the proximal end of the occlusion. Sonication of the blockage is then carried out for approximately 60-second intervals by transmitting ultrasonic energy from the energy source through the ultrasound transmission device to the tip. During sonication, the ultrasound transmission device is preferably kept stationary for the first approximately 30 to 60 seconds, and then moved slowly back and forth over approximately 3 mm. The blockage is thereby ablated by the cavitation.

In an alternative method, after locating the ultrasound transmission device in close contact with the occlusion and sonicating the thrombus for approximately 30 to 60 seconds, the user may attenuate the strands of the thrombus by modifying the handling of the probe. One means of attenuating the thrombus strands is to advance the tip in a stepwise motion through the thrombus while the tip is oscillating in a longitudinal direction. This action effectively pulls apart or mechanically disorganizes the blockage by utilizing a vortex to suck the blockage toward the tip as the tip is being withdrawn. Further, moving the tip toward and away from the obstruction can speed the ablation of the obstruction.

It is understood that the ultrasound transmission device and method for using the device shown and described herein is readily adapted to be guided in a human's blood vessel for the purpose of ablating unwanted material. The ultrasound transmission device may be utilized in different applications and therefore need not be limited solely to coronary angioplasty, nor even to medical applications.

It will thus be seen that the object set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An ultrasound transmission device constructed to be coupled to an ultrasound energy source, the device being dimensioned for insertion within a vessel or a body cavity to apply ultrasound energy to a selected location within the vessel or the body cavity, comprising:

at least one transmission member, having a proximal end, and a distal end having a transmission member diameter, said proximal end being dimensioned to connect to the ultrasound energy source; and a tip connected to the distal end of said at least one transmission member, the tip having a distal section, a proximal section and an intermediate section between the distal section and the proximal section, the proximal, distal and intermediate sections having a common longitudinal axis; the proximal section having a first diameter larger than the transmission diameter, the intermediate section having a decreasing step portion more narrow in diameter at a distal end than at a proximal end, a narrowed portion narrower in diameter than the diameter of the proximal end of the intermediate section and an increasing step portion which increases in diameter in the distal direction, and a distal section having a second diameter, the second diameter being less than said first diameter.

2. The ultrasound transmission device of claim 1, wherein the widest point of the narrowed portion has a third diameter and the second diameter is greater than the third diameter.

3. The ultrasound transmission device of claim 1, wherein the proximal section includes a body and at least one raised ring portion extending outwards about the circumference of the body.

4. The ultrasound transmission device of claim 3, wherein the proximal section includes a first raised ring portion, and a second raised ring portion spaced apart from the first ring along the direction of the longitudinal axis.

5. The ultrasound transmission device of claim 4, wherein the proximal section includes radially spaced apart raised supports extending generally parallel to the longitudinal axis from the first ring to the second ring.

6. The ultrasound transmission device of claim 1, wherein the proximal section includes at least one beveled surface.

7. The ultrasound transmission device of claim 1, wherein the decreasing step portion includes at least two steps.

8. The ultrasound transmission device of claim 1, wherein the increasing step portion includes at least two steps.

9. The ultrasound transmission device of claim 1, wherein the distal section has a generally hemispheroidal shape.

10. The ultrasound transmission device of claim 1, wherein the distal section has at least a first channel and a second channel spaced apart radially, the first channel and the second channel extending substantially parallel to the longitudinal axis.

11. The ultrasound transmission device of claim 1, wherein the proximal section includes at least one spiral channel extending in a direction oblique to the longitudinal axis.

12. The ultrasound transmission device of claim 1, wherein at least one of the decreasing step portion or the increasing step portion has a generally spiral orientation.

13. The ultrasound transmission device of claim 1, wherein the intermediate section includes an intermediate body having a fourth maximum diameter greater than the first diameter and the second diameter.

14. The ultrasound transmission device of claim 1, wherein the intermediate section includes an intermediate body having a fourth maximum diameter greater than the second diameter and less than the first diameter.

15. The ultrasound transmission device of claim 1, wherein the tip is constructed and dimensioned to cause cavitation, ablate, lyse or otherwise remove or loosen obstructing material within said blood vessel.

16. The ultrasound transmission device of claim 1, wherein the tip includes a through-hole for the passage of a guidewire.

17. The ultrasound transmission device of claim 16, wherein the through-hole is substantially aligned with the longitudinal axis of the tip.

18. The ultrasound transmission device of claim 1, wherein the tip includes a radiopaque material.

19. An ultrasound transmission device constructed to be coupled to an ultrasound energy source, the device being dimensioned for insertion within a vessel or a body cavity to apply ultrasound energy to a selected location within the vessel or the body cavity, comprising:

a first transmission section, having a proximal end, a distal end having a transmission section diameter, said proximal end being dimensioned to connect to the ultrasound energy source;

a second transmission section extending distally from the distal end of the first transmission section, the second section having an overall cross-sectional dimension smaller than the cross-sectional dimension of the distal portion of the first section;

a third transmission section coupled to the distal end of the second section, the third section including one or more parallel transmission wires, each wire having an overall cross-sectional dimension smaller than the cross-sectional dimension of the second section; and a tip connected to the distal end of said third transmission section, the tip having a distal section, a proximal section, and an intermediate section between the distal section and the proximal section, the proximal section having a first diameter larger than the transmission diameter, the intermediate section having a decreasing step portion more narrow in diameter at a distal end than at a proximal end, a narrowed portion narrower in diameter than the diameter of the proximal end of the intermediate section and an increasing step portion which increases in diameter in the distal direction, and a distal section having a second diameter, the second diameter being less than said first diameter.

20. The ultrasound transmission device of claim 19, wherein the tip is constructed and dimensioned to cause cavitation of lyse, ablate or otherwise removal or loosening of obstructing material within a blood vessel or cavity when activated.

21. An ultrasound transmission device constructed to be coupled to an ultrasound energy source, the device being dimensioned for insertion within a vessel or a body cavity to apply ultrasound energy to a selected location within the vessel or the body cavity and having a having a longitudinal axis, the device comprising:
   a first transmission member, having a proximal end, a distal end and a transmission diameter, said proximal end being dimensioned to connect to the ultrasound energy source;
   a second transmission member coupled to the distal end of the first transmission member, the second transmission member including at least two parallel transmission wires, each wire of the at least two transmission wires having a cross-sectional dimension smaller than the cross-sectional dimension of the first transmission member;
   a tip connected to the distal end of the second transmission member, the tip having a bore substantially aligned with the longitudinal axis; and
   a first guidewire tube partially disposed within the bore of the tip and connected to the tip to guide a guidewire as it passes through the tip and to prevent the guidewire from damaging the tip when the device is activated.

22. The ultrasound transmission device of claim 21, comprising a second guidewire tube coupled to the second transmission member, the second guidewire tube terminating proximal the tip.

23. The ultrasound transmission device of claim 21, wherein the second guidewire tube is substantially the same length as, and extends substantially parallel to, the at least two transmission wires.

24. The ultrasound transmission device of claim 23, wherein the at least two transmission wires are partially contained in sheathing, and the second guidewire tube is coupled to the sheathing of the at least two transmission wires.

25. The ultrasound transmission device of claim 21, wherein the second guidewire tube extends through a hole in the tip.

26. The ultrasound transmission device of claim 21, wherein the tip includes a through-hole through which a second guidewire tube assembly passes, the second guidewire tube assembly being slidably disposed relative to the first guidewire tube.

27. The ultrasound transmission device of claim 21, comprising sheathing, wherein the sheathing includes a single-lumen-to-multi-lumen joint so as to promote the passage of a fluid within the second transmission member.

28. The ultrasound transmission device of claim 21, comprising sheathing for containing the first and second transmission members and wherein the sheathing is attached to the first transmission member at a displacement minimum.

29. The ultrasound transmission device of claim 28, wherein the sheathing is attached to the first transmission member by means of an O-ring seal assembly.

30. The ultrasound transmission device of claim 29, wherein the O-ring seal assembly includes a keyed or shaped element that prevents independent rotation of the sheathing relative to the first and second transmission members.

31. A tip constructed to cause cavitation in a fluid upon application of ultrasound energy from a cavitation-causing ultrasonic transmission apparatus driven for longitudinal, reciprocating displacement, comprising a proximal section connectable to an ultrasonic transmitter, a distal section and an intermediate section for connecting said proximal and distal sections, the proximal and distal sections having respective diameters, and the intermediate section having a diameter smaller than the diameter of each of said proximal and distal sections, the proximal, distal and intermediate sections having a common longitudinal axis; the intermediate section having a decreasing step section, a narrowed portion and an increasing step portion.

32. An ultrasound transmission device constructed to be coupled to an ultrasound energy source, the device being dimensioned for insertion within a vessel or a body cavity to apply ultrasound energy to a select location within the vessel or the body cavity, comprising:
   at least one transmission member, having a proximal end and a distal end, said proximal end being dimensioned to connect to the ultrasound energy source at a location external the vessel or cavity; and
   a tip connected to the distal end of said at least one transmission member, the tip being formed of a polymer.

* * * * *